(12) United States Patent
Reddy et al.

(10) Patent No.: US 9,463,140 B2
(45) Date of Patent: Oct. 11, 2016

(54) DISPENSING DEVICE WITH TAMPER DETECTION

(71) Applicant: Abiogenix Inc., Rochester, MI (US)

(72) Inventors: Goutam Reddy, Rochester, MI (US); Sara Cinnamon, San Francisco, CA (US)

(73) Assignee: Abiogenix Inc., Rochester, MI (US)

( * ) Notice: Subject to any disclaimer, the term of this patent is extended or adjusted under 35 U.S.C. 154(b) by 0 days.

(21) Appl. No.: 14/455,618

(22) Filed: Aug. 8, 2014

(65) Prior Publication Data

US 2014/0339248 A1 Nov. 20, 2014

Related U.S. Application Data

(63) Continuation of application No. 14/377,583, filed as application No. PCT/US2013/025450 on Feb. 8, 2013.

(60) Provisional application No. 61/597,440, filed on Feb. 10, 2012.

(51) Int. Cl.
*B65D 83/04* (2006.01)
*A61J 7/00* (2006.01)
(Continued)

(52) U.S. Cl.
CPC .............. *A61J 7/0076* (2013.01); *A61J 7/0481* (2013.01); *B65D 83/0409* (2013.01); *G06F 19/3462* (2013.01); *A61J 7/0418* (2015.05); *A61J 2200/30* (2013.01); *A61J 2200/70* (2013.01); *A61J 2205/70* (2013.01)

(58) Field of Classification Search
CPC .......... B65D 83/0454; B65D 83/0463; B65D 83/0409; A61J 7/0076; A61J 7/0481; G06F 19/3462

USPC ................................ 221/113, 119, 120, 121
See application file for complete search history.

(56) References Cited

U.S. PATENT DOCUMENTS

| 4,068,661 A | 1/1978 | Hennings |
| 4,069,942 A | 1/1978 | Marshall et al. |
| 5,562,231 A | 10/1996 | Lambelet, Jr. et al. |

(Continued)

FOREIGN PATENT DOCUMENTS

EP 2338550 6/2011

OTHER PUBLICATIONS

"International Preliminary Report on Patentability and Search Report", International Application No. PCT/US2013/025450, May 30, 2013, 6 pages.

(Continued)

*Primary Examiner* — Patrick Mackey

(57) ABSTRACT

Embodiments generally relate to a pill box adapted for dispensing medication. In one embodiment, the pill box includes a base member, a carousel coupled to the base member and configured to rotate about the base member, one or more compartments, each compartment formed within the carousel and configured to store a single dose of medication with a lid configured to enclose the base and the carousel. The pill box ratchet advancement mechanism includes a resilient member and a stop member configured to facilitate motion of the carousel in a first direction and to restrict motion in a second direction, and a locking component configured to permit a pre-determined displacement of the carousel in the first direction and to limit further displacement in the first direction by locking the carousel.

15 Claims, 24 Drawing Sheets

(51) Int. Cl.
*A61J 7/04* (2006.01)
*G06F 19/00* (2011.01)

(56) References Cited

U.S. PATENT DOCUMENTS

| | | | |
|---|---|---|---|
| 6,048,087 A | 4/2000 | Laurent et al. | |
| 6,062,420 A | 5/2000 | Krouwel et al. | |
| 6,145,697 A | 11/2000 | Gudish | |
| 6,234,343 B1 | 5/2001 | Papp | |
| 6,415,202 B1 | 7/2002 | Halfacre | |
| 6,471,087 B1 | 10/2002 | Shusterman | |
| 6,601,729 B1* | 8/2003 | Papp | A61J 7/0084 206/528 |
| 6,948,492 B2 | 9/2005 | Wermeling et al. | |
| 7,108,153 B2 | 9/2006 | Wood | |
| 7,293,673 B2* | 11/2007 | Savage | A47B 88/00 221/119 |
| 7,359,765 B2 | 4/2008 | Varvarelis et al. | |
| 7,392,918 B2 | 7/2008 | Holloway et al. | |
| 7,978,564 B2 | 7/2011 | De La Huerga | |
| 8,777,895 B2 | 7/2014 | Hsu et al. | |
| 8,919,341 B2 | 12/2014 | Jung | |
| 2002/0093429 A1 | 7/2002 | Matsushita | |
| 2003/0127463 A1 | 7/2003 | Varis | |
| 2004/0206609 A1 | 10/2004 | Tilley | |
| 2005/0188853 A1* | 9/2005 | Scannell | A01G 9/02 96/417 |
| 2006/0021614 A1* | 2/2006 | Wermeling | A61M 11/06 128/200.14 |
| 2006/0215495 A1 | 9/2006 | Soled et al. | |
| 2008/0179387 A1* | 7/2008 | Cantlay | A61J 7/0481 235/375 |
| 2008/0203107 A1 | 8/2008 | Conley et al. | |
| 2009/0192648 A1 | 7/2009 | Namineni et al. | |
| 2011/0022224 A1 | 1/2011 | Park | |
| 2011/0140831 A1* | 6/2011 | Michael | A61J 7/0084 340/3.31 |
| 2011/0286008 A1* | 11/2011 | Schlaeppi | A61M 5/1456 356/614 |
| 2012/0035760 A1 | 2/2012 | Portney | |
| 2012/0278278 A1 | 11/2012 | Wester et al. | |
| 2013/0191513 A1 | 7/2013 | Kamen et al. | |
| 2013/0197693 A1 | 8/2013 | Kamen et al. | |
| 2013/0304255 A1 | 11/2013 | Ratnakar | |
| 2014/0097194 A1* | 4/2014 | Lai | B65D 83/0454 221/13 |
| 2015/0232256 A1* | 8/2015 | Hoover | G06F 19/3462 700/236 |

OTHER PUBLICATIONS

"International Search Report", International Application No. PCT/US2013/025450, May 30, 2013, 3 pages.

"Non-Final Rejection", U.S. Appl. No. 14/455,647, Oct. 6, 2015, 8 pages.

"Non-Final Rejection", U.S. Appl. No. 14/377,583, Oct. 8, 2015, 8 pages.

"Non-Final Rejection", U.S. Appl. No. 14/455,635, Dec. 30, 2015, 7 pages.

"Non-Final Office Action", cited in U.S. Appl. No. 14/377,583, Apr. 27, 2016.

"Final Office Action", cited in U.S. Appl. No. 14/455,635, Jun. 6, 2016.

"Notice of Allowance", cited in U.S. Appl. No. 14/455,635, Jun. 21, 2016.

"Final Office Action", cited in U.S. Appl. No. 14/455,647, Apr. 29, 2016.

* cited by examiner

STATE 1

STATE 3

STATE 2

STATE 4

Accessing Device 11392 Interaction Log

| MDD ID | Date | Time |
|---|---|---|
| 89393 | 12-02-2002 | 8:30AM |
| 12932 | 12-02-2002 | 9:03AM |
| 18133 | 12-02-2002 | 9:37AM |
| 12932 | 12-02-2002 | 12:03PM |
| 8202 | 12-02-2002 | 4:20PM |
| 89393 | 13-02-2002 | 8:25AM |
| 12932 | 13-02-2002 | 8:47AM |
| 18133 | 13-02-2002 | 9:12AM |
| 12932 | 13-02-2002 | 11:47AM |
| 8202 | 13-02-2002 | 4:04PM |
| 89393 | 14-02-2002 | 8:40AM |
| 12932 | 14-02-2002 | 9:14AM |
| 18133 | 14-02-2002 | 9:56AM |
| 12932 | 14-02-2002 | 11:58AM |
| 8202 | 14-02-2002 | 4:15PM |

Dispensing Device 89393 Interaction Log

| AD ID | Date | Time |
|---|---|---|
| 11392 | 12-02-2002 | 8:30AM |
| 8923 | 12-02-2002 | 4:50PM |
| 11392 | 13-02-2002 | 8:25AM |
| 8923 | 13-02-2002 | 4:55PM |
| 11392 | 14-02-2002 | 8:40AM |
| 8923 | 14-02-2002 | 5:03PM |

FIG. 23

DISPENSING DEVICE WITH TAMPER DETECTION

The present application claims priority to U.S. Nonprovisional patent application Ser. No. 14/377,583, filed on 8 Aug. 2014, which claims priority to Patent Cooperation Treaty application No. PCT/US2013/025450, filed on 8 Feb. 2013, which claims priority to U.S. Provisional patent application No. 61/597,440, filed on 10 Feb., 2012, which are hereby incorporated by reference as if set forth in full in the application for all purposes.

BACKGROUND

Healthcare today is implemented as an open-loop system. Patients are diagnosed by a physician and prescribed treatment. However, there are not many reliable systems capable of monitoring whether the patient is complying with or adhering to the instructions given by the physician. Studies have shown that if patients stop taking their medication for three days, they are unlikely to resume their regimen.

Patients may access the wrong medications at the wrong times. Patients may double-dose on medication if they forgot they have already taken their prescribed dose. Children, and other unauthorized users, can break-in to existing pill-containers and remove pills. Patients can intentionally overdose on medications. There is a large problem of diversion with controlled substances such as pain medications or opioid-withdrawal medication, such that patients sometimes illicitly sell or give away these medications in bulk.

One approach to ensure adherence to medical prescriptions is the use of various medicine-dispensing devices for dispensing medicines to users. Such devices typically have multiple compartments for storing medicines. While some of these medical dispensing devices can be programmed to dispense medicines at an appropriate medication schedule, a user can access multiple compartments of the device at the same time.

Healthcare workers at a medical facility are typically entrusted with the task of monitoring patients within the facility. Typically, healthcare workers use a time clock to record the time of day on a medication record when interacting with a patient. However, because this is a manual mechanism, there may be potential for inaccuracies. Moreover, manual mechanisms or systems may not be an efficient way to monitor a patient's adherence rate.

Additionally, interaction monitoring is important in situations where a healthcare provider is interacting with patients. A central monitoring system can be used to determine whether the healthcare worker is performing his/her duties. One example includes a nurse or orderly in a nursing home environment who must do daily rounds. Another example is a healthcare worker taking part in a DOTS (Directly Observed Treatment, Short-course) program, such as is used in many tuberculosis treatments. This approach can be applied to any scenario where one person must interact with several others and this interaction may need to be monitored.

Current monitoring systems include computerized attendance systems that can read a unique employee number and other data from an identification badge when the employee arrives and departs the workplace. The acquired employee identification data are transmitted and recorded in a central monitoring device along with the current date and time. However, such systems may not be capable of recording the state of the patient's adherence rate unless manually entered by the healthcare worker.

SUMMARY

Embodiments generally relate to a pill box adapted for dispensing medication. In one embodiment, the pill box includes a base member, a carousel coupled to the base member and configured to rotate about the base member, one or more compartments, each compartment formed within the carousel and configured to store a single dose of medication with a lid configured to enclose the base and the carousel. The pill box ratchet advancement mechanism includes a resilient member and a stop member configured to facilitate motion of the carousel in a first direction and to restrict motion in a second direction, and a locking component configured to permit a pre-determined displacement of the carousel in the first direction and to limit further displacement in the first direction by locking the carousel.

With further regard to the pill box, in one embodiment, the stop member is formed on a wall of the base member. With further regard to the pill box, in one embodiment, fins are disposed around the carousel and distal portion of the fin, includes the resilient member. With further regard to the pill box, in one embodiment, includes fins disposed around the carousel, and distal portion of the fin, includes the resilient member, and the stop member is formed on a wall of the base member. With further regard to the pill box, in one embodiment, the stop member is formed on the lid.

In another embodiment, the dispensing device includes a base member, a carousel coupled to the base member and configured to rotate about the base member, one or more compartments, each compartment formed within the carousel, and an access control mechanism operatively coupled to the carousel and the base member and configured to regulate a motion of the carousel and to selectively permit access to the compartments.

With further regard to the dispensing device, in one embodiment, the access control mechanism includes a locking component configured to permit a predetermined displacement of the carousel in a first direction and to limit further displacement in the first direction. In an embodiment, the locking component includes a linear actuator configured to move linearly and limit rotation of the carousel. In an embodiment, the linear actuator includes a motor, a worm comprising one or more grooves and mounted axially on the motor, and a rack gear configured to interface with the worm by means of one or more grooves, and rotation of the worm causes a linear movement of the rack gear, to permit a pre-determined displacement of the carousel in a first direction and to limit further displacement in the first direction. With further regard to the dispensing device, in one embodiment, the access control mechanism includes electronic circuitry configured to limit and record rotation of the carousel. With further regard to the dispensing device, in one embodiment, the access control mechanism comprises a locking component configured to permit a predetermined displacement of the carousel, and the locking component includes a linear actuator configured to move linearly and limit rotation of the carousel, when the linear actuator includes a motor, a worm including grooves and mounted axially on the motor. The dispensing device includes a rack gear configured to interface with the worm by means of the grooves, when a rotation of the worm causes a linear movement of the rack gear, to permit a pre-determined displacement of the carousel in a first direction and to limit further displacement in the first direction, and when the electronic circuitry includes tracking means coupled to the rack gear and configured to track a position of the rack gear. With further regard to the dispensing device, in one embodiment, the access control mechanism further includes a ratchet advancement mechanism formed by a resilient member and a stop member, and the ratchet advancement mechanism is configured to facilitate motion of the carousel in a first direction and to restrict motion in a second direction.

In an embodiment, a dispensing device adapted for storing and dispensing articles, the device includes a base member, a carousel coupled to the base member and configured to rotate about the base member, compartments, each compartment formed within the carousel, and the carousel and the base member form a ratchet advancement mechanism configured to facilitate motion of the carousel in a first direction and to restrict motion in a second direction.

With further regard to the dispensing device, in another embodiment, a locking component disposed on the base member and configured to permit a pre-determined displacement of the carousel in the first direction and to limit further displacement in the first direction. With further regard to the dispensing device, in one embodiment, the locking component includes a linear actuator configured to move linearly and control rotation of the carousel, and the linear actuator includes a motor, a worm including one or more grooves and mounted axially on the motor and a rack gear configured to interface with the worm by means of the one or more grooves, when a rotation of the worm causes a linear movement of the rack gear. With further regard to the dispensing device, in an embodiment the carousel further includes a hollow shaft coupled to the center of the base member and one or more fins coupled to the shaft, when each fin extends outwards from the shaft to form a curved wall. With further regard to the dispensing device, in an embodiment, the base member comprises an inner wall and, when the inner wall includes one or more ramps. With further regard to the dispensing device, in an embodiment, the one or more compartments are self-contained. With further regard to the dispensing device, in an embodiment, the carousel further includes a hollow shaft coupled to the center of the base member, and a spindle operatively coupled to the hollow shaft of the carousel and configured to facilitate rotation of the carousel. With further regard to the dispensing device, in another embodiment, further includes a handle operatively coupled to the carousel and configured to enable a user to rotate the carousel to dispense an article stored inside the compartment, a lid configured to enclose the carousel and a window disposed on the lid and configured to enable a user to access articles stored inside each compartment.

Embodiments generally relate to a dispensing device including a base member, a carousel coupled to the base member and configured to rotate about the base member, a cover disposed on a top portion of the carousel, and a securing mechanism disposed on the dispensing device and configured to prevent unauthorized access to contents stored within the dispensing device.

With further regard to the dispensing device, in one embodiment, the securing mechanism includes a tamper detection device operatively coupled to the cover or the base member and configured to generate an alarm signal in response to displacement of the cover. With further regard to the dispensing device, in one embodiment, the securing mechanism includes a tamper detection device operatively coupled to the cover or the base member and configured to generate an alarm signal in response to displacement of the cover and further including a linking component coupled to the tamper detection device, and the tamper detection device is configured to generate the alarm signal when the linking component is decoupled from the tamper detection device. With further regard to the dispensing device, in one embodiment, the securing mechanism includes a tamper detection device operatively coupled to the cover or the base member and configured to generate an alarm signal in response to displacement of the cover and further including a linking component coupled to the tamper detection device, and the tamper detection device is configured to generate the alarm signal when the linking component is decoupled from the tamper detection device and when the linking component includes an electronic device or a mechanical component. With further regard to the dispensing device, in one embodiment, the securing mechanism includes a tamper detection device operatively coupled to the cover or the base member and configured to generate an alarm signal in response to displacement of the cover, and includes a linking component coupled to the tamper detection device and the tamper detection device is configured to generate the alarm signal when the linking component is decoupled from the tamper detection device. In an embodiment the linking component includes a magnet, and upon displacement of the cover, the tamper detection device is configured to detect a change in electromagnetic field generated by the magnet. With further regard to the dispensing device, in one embodiment, the securing mechanism comprises a tamper detection device operatively coupled to the cover or the base member and configured to generate an alarm signal in response to displacement of the cover further including a linking component coupled to the tamper detection device. In an embodiment, the tamper detection device is configured to generate the alarm signal when the linking component is decoupled from the tamper detection device and processing circuitry disposed within the dispensing device and configured to record a time at which the linking component is decoupled from the tamper detection device. With further regard to the dispensing device, in one embodiment, the securing mechanism includes a tamper detection device operatively coupled to the cover or the base member and configured to generate an alarm signal in response to displacement of the cover, further including a linking component coupled to the tamper detection device and the tamper detection device is configured to generate the alarm signal when the linking component is decoupled from the tamper detection device, and processing circuitry disposed within the dispensing device and configured to record a time at which the linking component is decoupled from the tamper detection device and the processing circuitry is configured to transmit a time log and the time log includes a first time at which the cover was displaced and a second time at which the carousel was rotated. With further regard to the dispensing device, in one embodiment, a lid configured to enclose the base member and the carousel, when the cover is disposed on the lid. With further regard to the dispensing device, in one embodiment, the securing mechanism includes a security component formed by an inner wall extending upwards from a base plate of the base member, and an outer wall of the lid and the inner wall of the base member and outer wall of the lid overlap when enclosing the carousel. With further regard to the dispensing device, in one embodiment, the securing mechanism includes a security fastener configured to mechanically fasten the cover to the base member. With further regard to the dispensing device, in one embodiment, the securing mechanism includes visual indicators disposed on the dispensing device.

In an embodiment, a dispensing device includes a base member, a carousel coupled to the base member and configured to rotate about the base member, a lid configured to enclose the base member and the carousel, a cover disposed on the lid, and a tamper detection device including a electromechanical component disposed within the dispensing device and a electromechanical sensor corresponding to the electromechanical component and configured to generate an alarm signal in response to displacement of the cover.

With further regard to the dispensing device, in one embodiment, the electromechanical component is a magnet and electromechanical sensor is a magnetic sensor, and when the magnetic sensor is configured to detect a change in electromagnetic field generated by the magnet in response to the displacement of the cover. With further regard to the dispensing device, in one embodiment, the electromechanical component is an optical emitter and electromechanical sensor is an optical sensor, when the optical sensor is configured to detect an optical change in optical path of the optical emitter in response to the displacement of the cover. With further regard to the dispensing device, in one embodiment, processing circuitry is disposed within the dispensing device and configured to store a time log, when the time log includes a time at which the cover was displaced.

In another embodiment, a method for detecting unauthorized access to a pill box, the method includes creating an electromechanical link between a first component and a second component of the pill box, detecting a change in the electromechanical link, when the change is indicative of a displacement of the first component with respect to the second component from their respective initial positions and generating an alarm signal in response to the change in the electromechanical link.

With further regard to the method, in an embodiment, creating the electromechanical link includes creating an electromagnetic field using a magnet, and detecting the change in the electromechanical link including detecting a change in the electromagnetic field using a magnetic sensor. With further regard to the method, in an embodiment, creating the electromechanical link comprises creating an optical path using at least one optical emitter, wherein detecting the change in the electromechanical link includes detecting an optical change using an optical sensor. With further regard to the method, in an embodiment, the alarm signal includes an acoustic indicator signal or an optical indicator signal. With further regard to the method, in an embodiment, the method includes recording a time log corresponding to the change in the electromechanical link and transferring the time log to a computing device.

Embodiments generally relate to a central monitoring system for monitoring one or more dispensing devices. In an embodiment, the central monitoring system includes accessing devices configured to provide access to dispensing devices. In an embodiment the accessing devices include a transceiver configured to transmit an identity tag to the dispensing devices when disposed adjacent to the dispensing devices, which contain memory circuitry configured to store the identity tag. In an embodiment the central monitoring system includes computing devices that include an analysis module configured to receive identity tags from the one or more dispensing devices, and process each identity tag to identify the one or more dispensing devices accessed by the one or more accessing devices.

With further regard to the central monitoring system, in one embodiment, the central monitoring system includes a transceiver configured to receive device data from the dispensing devices. With further regard to the central monitoring system, in one embodiment, the central monitoring system receives a time stamp providing the time dispensing devices are accessed by the accessing devices. In an embodiment, each accessing device is configured to be mechanically coupled to the dispensing devices. In another embodiment, each accessing device is configured to be electronically coupled to the dispensing devices. With further regard to the central monitoring system, in one embodiment, the central monitoring system monitors/records device data that includes one or more of dose dispensation data, doses remaining data, regimen data, ambient temperature data, battery level data, time of dispensation data, reset data, and accessory-device access data. In an embodiment, the analysis module is further configured to analyze device data received from the dispensing devices. In another embodiment, the central monitoring system is configured to transmit an alert to a secondary central monitoring system; the alert is based upon the device data analyzed by the analysis module and the secondary central monitoring systems are associated with the dispensing devices. With further regard to the central monitoring system, in one embodiment, each accessing device is further configured to unlock and lock the dispensing devices.

In another embodiment, an accessing device is adapted for use with medication dispensing devices, the accessing device includes a transceiver configured to transmit an identity tag to the medication dispensing devices when disposed adjacent to the medication dispensing devices with memory circuitry configured to store the identity tag, and the accessing device is adapted to unlock or lock the one or more medication dispensing devices.

With further regard to the accessing device, in one embodiment, the accessing device includes a transceiver configured to receive device data from the medication dispensing devices. In an embodiment, the transceiver is configured to transmit data to the one or more medication dispensing devices. With further regard to the accessing device, in one embodiment, the accessing device includes indicators configured to be enabled when the identity tag is matched with a reference tag stored in the medication dispensing devices. With further regard to the accessing device, in one embodiment, the accessing device includes a communication portal configured to transmit device data to the central monitoring systems.

In an embodiment, a method for monitoring dispensing devices in a healthcare network includes accessing dispensing devices using an accessing device, transmitting an identity tag to each dispensing device, and storing the identity tag in memory circuitry disposed within each dispensing device. In an embodiment the method includes transferring the identity tag to the computing devices, processing the identity tag to determine device interaction status of each dispensing device, and reporting the device state of each dispensing device distributed in the healthcare network.

With further regard to the method, in one embodiment, the method includes receiving device data from the dispensing devices using the accessing device and reporting the device data of the dispensing devices. With further regard to the method, in one embodiment, the method includes transmitting alerts based upon the device data to secondary central monitoring systems, and the secondary central monitoring systems are associated with the dispensing devices. In an embodiment, the method includes analyzing device data received from the dispensing devices to determine an adherence rate of the one or more dispensing devices. In another embodiment, the method includes analyzing the device state of the dispensing devices to determine an operational condition of the dispensing devices. In another embodiment, the method includes analyzing the device data to determine prescription data for the dispensing devices.

Embodiments generally relate to a dispensing device adapted for storing and dispensing articles. In one embodiment, the dispensing device includes a base member, a carousel coupled to the base member and configured to rotate about the base member, a plurality of compartments, each compartment formed within the carousel and configured to store a plurality of articles. The dispensing device may also include a dispensation detection system including sensors disposed within the dispensing device and configured to generate a signal corresponding to a displacement of the carousel with respect to the base member, and processing circuitry coupled to the dispensation detection system and configured to receive the signal generated by the dispensation detection system and record a time at which the signal was received.

With further regard to the dispensing device, in one embodiment, the sensors include an electromechanical device coupled to the base member and configured to detect a displacement of the carousel. With further regard to the dispensing device, in one embodiment, the sensors include at least one infrared detector coupled to the base member and configured to detect a displacement of the carousel. With further regard to the dispensing device, in one embodiment, the sensors include at least one mechanical switch configured to alternate between an enabled state and a disabled state, each state change corresponding to a displacement of the carousel by one compartment. With further regard to the dispensing device, in one embodiment, the sensors include magnets and magnetic sensors configured to detect a change in the electromagnetic field generated by the magnets. In another embodiment, the dispensing device includes magnets and magnetic sensors configured to detect a change in the electromagnetic field generated by the magnets, when the number of magnets is less than or equal to a number of compartments and when a number of magnetic sensors is different from the number of magnets. With further regard to the dispensing device, in one embodiment, the sensors include optical sensors coupled to the base member and configured to sense a change in a reflective pattern disposed on a wall of each compartment. With further regard to the dispensing device, in one embodiment, the processing circuitry is configured to generate a reminder signal at predetermined time. With further regard to the dispensing device, in one embodiment, each compartment is identified with a unique identifier and upon rotation of the carousel, the processing circuitry is configured to execute an encoding scheme to determine the unique identifier.

In another embodiment, the dispensing device is adapted for storing and dispensing articles, and includes a base member, a carousel coupled to the base member including compartments. Each compartment comprises a unique identifier and the carousel is configured to rotate about the base member to provide access to one compartment per rotation. The dispensing device further includes a dispensation detection system disposed within the carousel and configured to generate a signal corresponding to a rotation of the carousel with respect to the base member, and processing circuitry coupled to the dispensation detection system and configured to: receive the signal generated by the dispensation detection system, identify the unique identifier of the accessed compartment according to an encoding scheme, and record a time at which the signal was received, for each rotation of the carousel.

With further regard to the dispensing device, in one embodiment, the dispensation detection system includes magnets on the carousel and magnetic sensors on the base configured to detect a magnetic field generated by the magnets. In another embodiment, the dispensing device includes magnets on the carousel and a plurality of magnetic sensors on the base configured to detect a magnetic field generated by the magnets, when the number of magnets is less than or equal to a number of compartments and when the number of magnetic sensors is different from the number of magnets. With further regard to the dispensing device, in one embodiment, the unique identifier of each compartment corresponds to a four-bit code. In another embodiment, the unique identifier of each compartment corresponds to a grayscale value. With further regard to the dispensing device, in one embodiment, the dispensation detection system includes optoelectronic sensors disposed on the base and a plurality of markers on the carousel.

In an embodiment, a method for detecting dispensation of medication adapted for use in a medication dispensing device includes compartments. The method further includes generating an indicator signal corresponding to a displaced compartment, processing the indicator signal to identify a unique identifier of the displaced compartment based on an encoding scheme, and recording compartment displacement information corresponding to the displaced compartment.

With further regard to the method, in one embodiment, each unique identifier is a four-bit code. In another embodiment, each unique identifier is a gray scale value. With further regard to the method, in one embodiment, the method includes determining a state of each compartment using an optoelectronic system. With further regard to the method, in one embodiment, the method includes generating an indicator using electromechanical sensing devices to indicate a state of a compartment.

DRAWINGS

FIG. 23 is an example of a displayed output of a time-log of interactions between an accessing device and medication dispensing devices for an example scenario.

DETAILED DESCRIPTION

Embodiments described herein provide a dispensing device (e.g. a pill box) for dispensing medication. In various embodiments, the dispensing device may include a base member, a carousel coupled to the base member and configured to rotate about the base member. In some embodiments, the dispensing device may include one or more compartments formed within the carousel and configured to store a single dose of medication. In some embodiments, the dispensing device includes a lid configured to enclose the base and the carousel.

Embodiments may include a ratchet advancement mechanism that includes a resilient member and a stop member configured to facilitate motion of the carousel in a first direction and to restrict motion in a second direction. In some embodiments, the dispensing device may include a locking component configured to permit a predetermined displacement of the carousel in the first direction and to limit further displacement in the first direction by locking the carousel.

The dispensing device may be utilized for storing medication such as but not limited to pills, capsules, ampules, dose-packs, vials, vitamins, gels, injectables, and creams. However, the dispensing device may also be used to store pet food, snacks (e.g., candy or gum), nutritional supplements, patches (e.g., nicotine or birth control), sublingual strips, prizes (e.g., stickers or marbles), reminder messages (e.g., hand-written notes), instructions for a scavenger hunt or daily operation of machinery, encrypted codes for logging in each day, etc. The dispensing device may be mounted on a wall for tracking when the handle is rotated, (and then possibly unlocking a door with this information).

Figure 1:
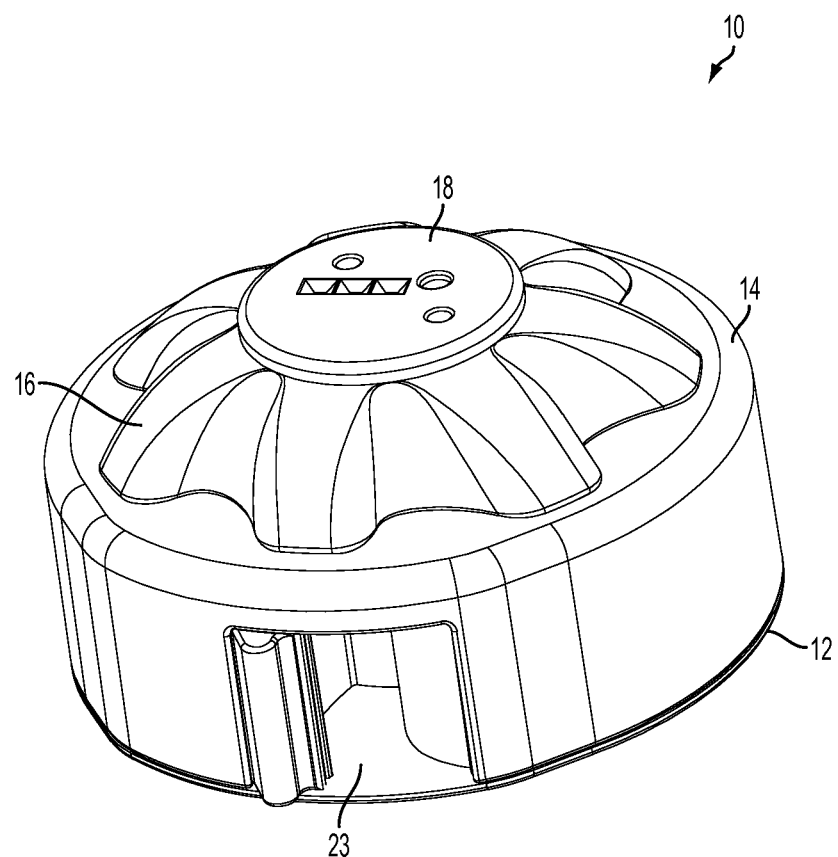
FIG. 1 is a perspective view of an example embodiment of a dispensing device.
Figure 2:
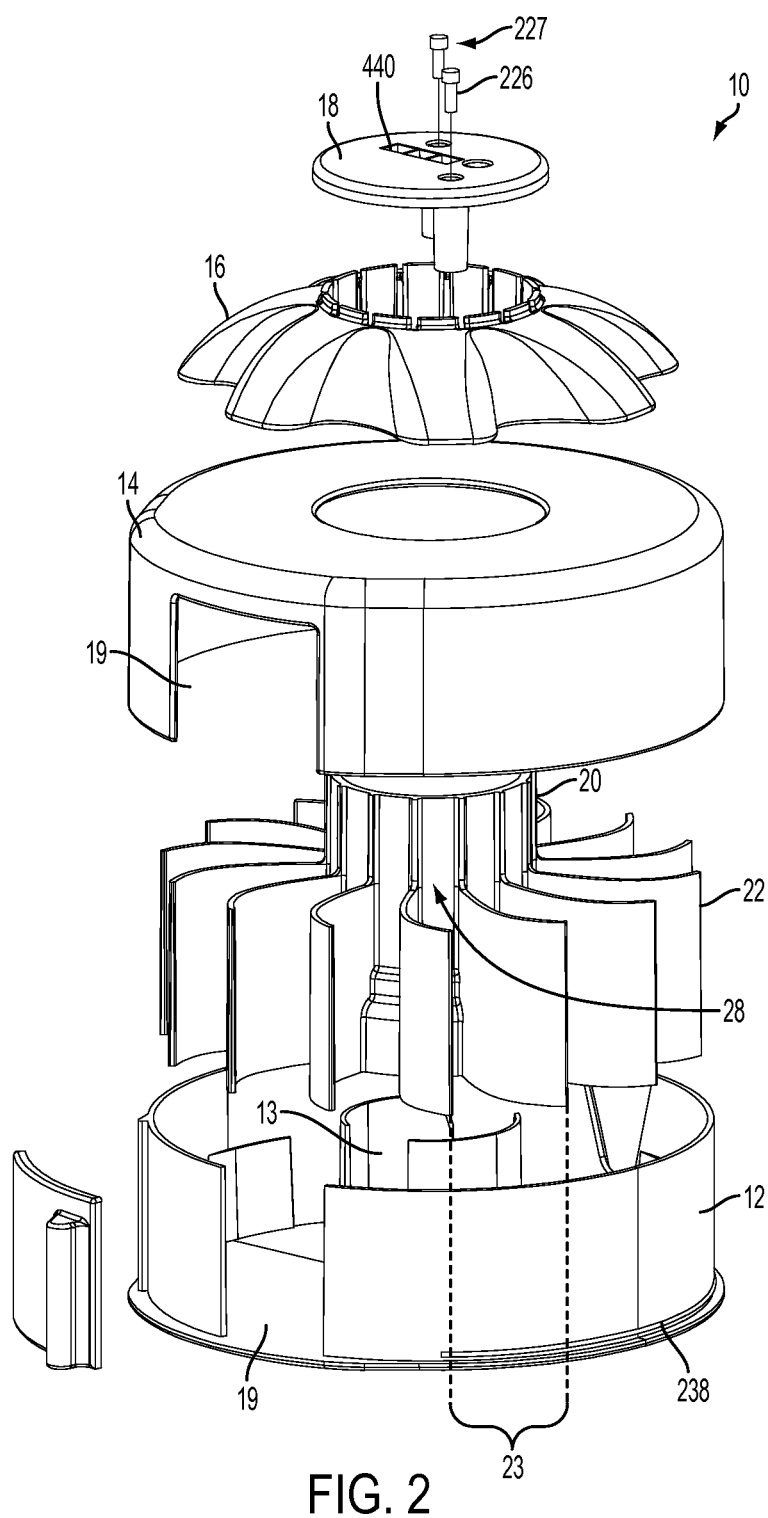
FIG. 2 is an exploded view of an example embodiment of a dispensing device.

Referring to FIGS. 1 and 2, an example embodiment of a dispensing device 10 is illustrated. The dispensing device 10 includes a base member 12, a lid 14, a handle 16 disposed over the lid 14 and a cover 18 disposed over the handle 16. The dispensing device 10 includes a carousel 20 that is configured to rotate at the base member 12. The articles stored in the dispensing device 10 can be accessed through a window 19.

FIG. 2 is an exploded view of an embodiment of a dispensing device 10. The base member 12 is coupled to a carousel 20 at the center of the base member 12. In one embodiment, the base member 12 comprises a spindle 13 that is operatively coupled to a shaft 28 of the carousel 20 and configured to facilitate rotation of the carousel 20. The carousel 20 further includes a plurality of fins 22 coupled to the shaft 28, each fin 22 extending outwards from the shaft 28 to form a curved wall. The compartments 23 are formed by an area formed between two consecutive fins 22 and a portion of the inner wall of the base member 12.

In some implementations, the compartments 23 may be formed by self-contained units instead of being defined by the walls of the carousel. In some implementations these self-contained units may contain indentations similar to a bundt pan shape. In other implementations the compartments 23 may be formed from fins that extend from the base member 12 to the shaft 28.

The access control mechanism is operatively coupled to the carousel 20 and the base member 12 and is configured to regulate a motion of the carousel 20 and to control access to the compartments 23. In one embodiment, the access control mechanism includes a ratchet advancement mechanism, a locking component 32, and electronic circuitry.

Figure 3:
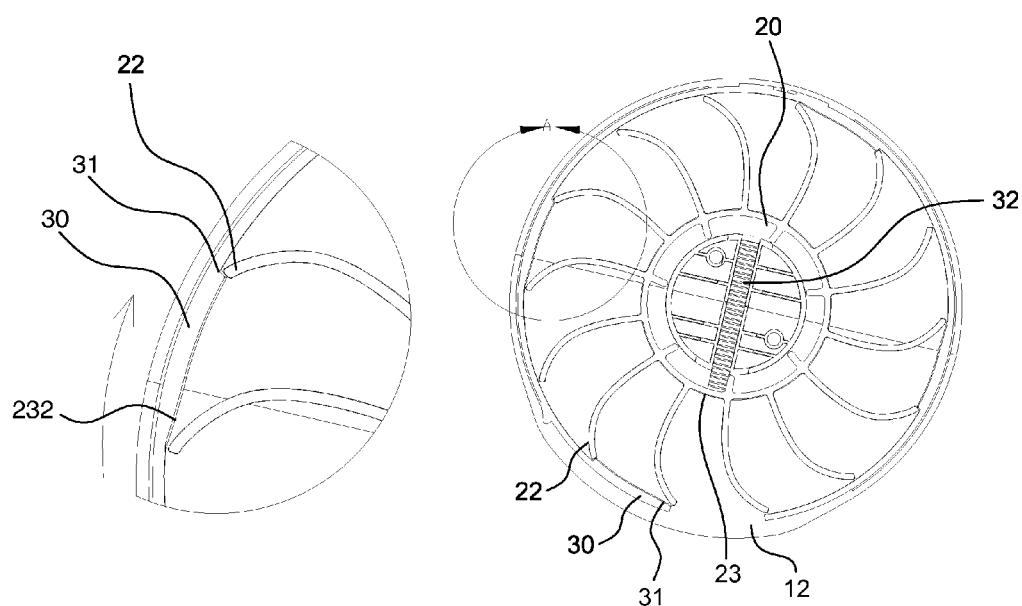
FIG. 3 is a top view of an example embodiment of a ratchet advancement mechanism.

Referring to FIG. 3, the ratchet advancement mechanism may be formed by a resilient member and a stop member. In some implementations the resilient member is formed by a distal portion of the fins 22 and the stop member is formed by a containing wall 232 on the inner wall of the base member 12. The ratchet advancement mechanism is configured to facilitate motion of the carousel 20 in the first direction, for example, a clockwise direction and to restrict motion in a second direction, for example, a counterclockwise direction.

In this example embodiment, as the carousel 20 is rotated, the edge of the fin 22 rides up a ramp 30 located on the inside of the wall 232. At the end of the ramp 30, there is a drop-off 31. The fin 22 passes over this drop-off and un-flexes, resting against the containing wall 13 and the face of the drop-off 31 in a way that the carousel 20 cannot be rotated in the counter-clockwise direction. In one embodiment, the length of a single ramp 30 may be referred as a ratchet tooth. In some implementations, the distance traveled per ratchet tooth corresponds to that needed to advance the carousel 20 one compartment. In other implementations, depending upon the number of compartments and the configuration, one ratchet tooth may correspond to a fraction or multiple of one compartment 23.

It may be noted that, the movement of the carousel 20 can be in one direction only, clockwise in this non-limiting example. This ensures proper sequence of the medication regimen, so that the user cannot accidentally back-drive the system to a compartment that has already been emptied. The ratchet advancement mechanism works in conjunction with a locking component 32, which is described in further detail below.

Figure 4:
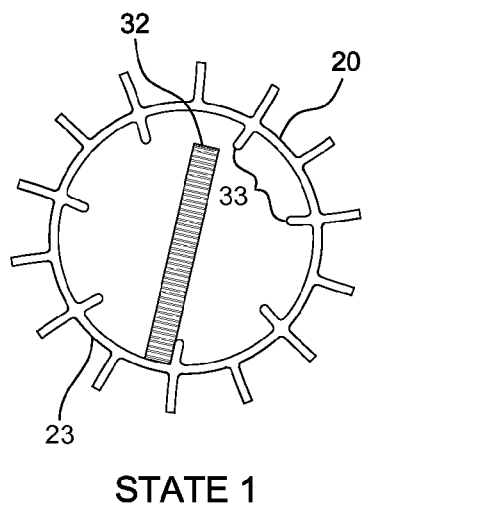
FIG. 4 is a top view of an example embodiment of a locking component.
Figure 4:
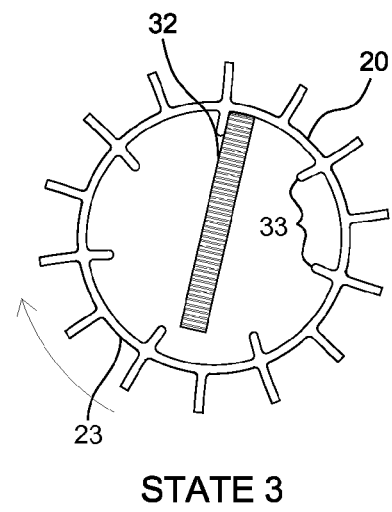
Figure 4:
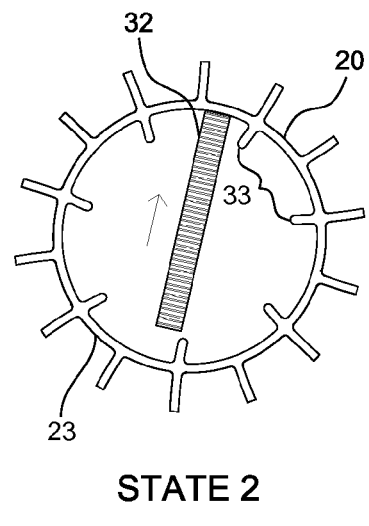
Figure 4:
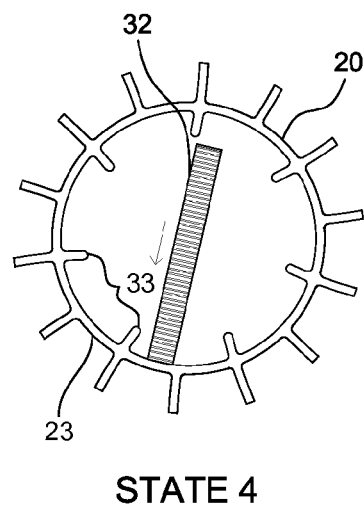

FIG. 4 is a perspective view schematically illustrating an embodiment of a locking component 32 of the access control mechanism in four example states. As described in FIG. 3, the ratchet advancement mechanism facilitates motion in a first direction. The locking component 32 works in conjunction with the ratchet advancement mechanism of FIG. 3 to permit a pre-determined displacement of the carousel 20 in a first direction and to limit further displacement in the first direction.

In one embodiment, the locking component 32 is a linear actuator that is moved linearly from one detent 33 to another diametrically opposite on an internal face of the carousel 20. Each detent 33 is a space formed by the inner faces of the carousel 20, and allows the carousel 20 to advance by one compartment before being engaged against the lateral face of the locking component 32. The locking component 32 may have four states as follows:

State 1 corresponds to the locking component 32 in the forward position and the carousel 20 having been rotated in a clockwise direction until the detent 33 on the inner face of the carousel 20 comes in contact with the lateral face of the locking component 32.

State 2 corresponds to the locking component 32 in the rear position and the carousel 20 unmoved. Clockwise motion of the carousel 20 is no longer impeded, and advancement by one compartment 23, and only one compartment 23, is possible.

State 3 corresponds to the locking component 32 in the rear position and the carousel 20 having been rotated in a clockwise manner until the detent 33 on the inner face of the carousel 20 comes in contact with the other face of the lock. The system is again locked and will not allow for further advancement of the carousel 20.

State 4 corresponds to the locking component 32 in the forward position again and the carousel 20 unmoved. Once again, clockwise motion of the carousel 20 is possible, in this case as a means for dispensing the next dose, but only one dose.

As seen in the four example states of FIG. 4, if both clockwise and counterclockwise motion of the carousel 20 is permitted, locking to a single compartment would not be achieved, and it would be possible for the user to go between and access two adjacent compartments 23 at will. Thus, in an example implementation the locking component 32 is configured to permit a predetermined displacement of the carousel 20 in only a first direction. Further, the locking component 32 works in conjunction with the ratchet advancement mechanism to limit further displacement in the first direction.

In this non-limiting example, the motion to advance the carousel 20 by one compartment is performed manually. As described above, the locking component 32 is achieved by moving a linear actuator diametrically across the inner region of the carousel 20. In other embodiments this motion could be performed automatically, for example using a solenoid, a linkage system, a gearing system, a voice coil, springs, piezoelectric actuators, a motor, or some combination thereof.

Figure 5:
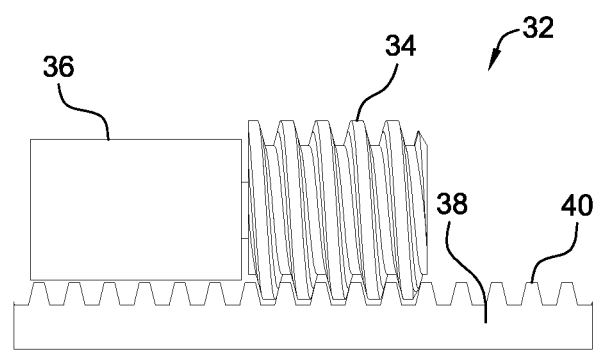
FIG. 5 is a diagrammatic view of an example embodiment of a linear actuator.

In one embodiment, the locking component 32 comprises a linear actuator configured to move linearly and control rotation of the carousel 20. FIG. 5 is a diagrammatic view of an embodiment of a linear actuator 32 implemented in a dispensing device. The linear actuator includes a worm 34 mounted axially on a motor shaft (not shown). The worm 34 then interfaces with a rack gear 38, which is mounted in a groove parallel to the worm 34 axis, such that the teeth 40 of the rack gear 38 engage the worm 34, and rotation of the worm 34 moves the rack gear 38 back and forth along the axis.

In this example embodiment, the rack gear 38 is specified to have a pitch of 32 and pressure angle of 14.5 degrees. The worm 34 is also specified to have a pitch of 32 and a pressure angle of 14.5 degrees, plus a lead angle of 4.08 degrees. A rack with a matching helical angle could also be used. Each gear may be made from plastic, metal, phenolic, or other material. The motor is specified such that its diameter is less than the pitch diameter of the worm 34 so that it does not interfere with the range of travel of the rack. It may or may not include a gearbox (not shown) to amplify the torque output. One such motor is the brushed DC micro motor by Autom.

In one embodiment, the actuator is compact and has a high torque ratio. An example non-limiting torque ratio is 150:1, or an output torque of 6 mNm. The gearing system is not back-drivable or possible to overcome via brute force without damaging the pill box. The forces on the rack due to the carousel 20 attempting to turn are not transmitted to the worm 34 or the motor 36, protecting them from damage.

In an example scenario, closed-loop control of the motor 36 in the locking system allows for self-calibration, whereas both open-loop and closed-loop control allow overcoming of stiction. In an embodiment, the motor control algorithm includes turning on the motor 36 in a particular direction for a predetermined set of time (e.g. 2 seconds). In one embodiment, motor speed is controlled using PWM (pulse-width modulation). Using PWM, a burst of speed can be provided at the beginning of the motor-on cycle (e.g. 100% PWM for 0.2 seconds) before reducing to a slower speed, in order to overcome stiction. In another embodiment, closed-loop control is employed to provide feedback to the rack's position in order to determine if the box is locked.

Figure 6:
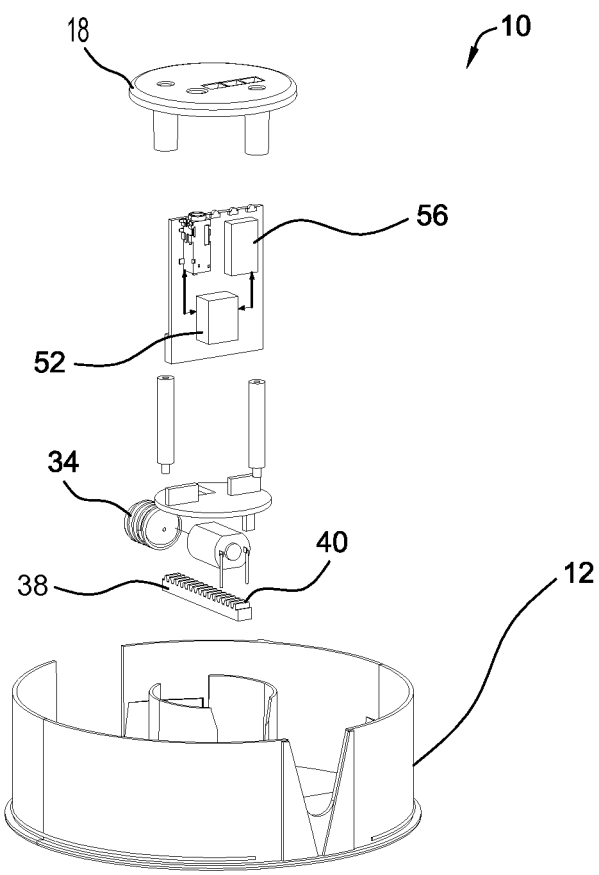
FIG. 6 and FIG. 7 are diagrammatic views of example embodiments of electronic circuitry disposed in the dispensing device.
Figure 7:
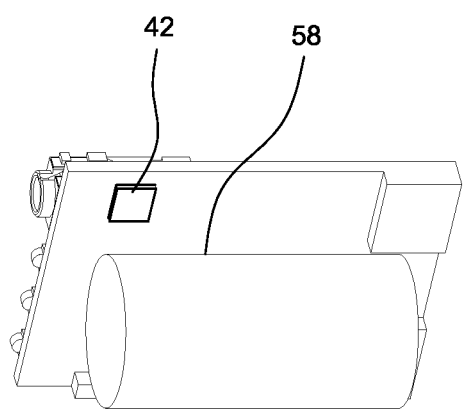

FIG. 6 and FIG. 7 are diagrammatic views of electronic circuitry configured to control and record rotation of the carousel 20. An example microcontroller 56 is configured to execute instructions that are programmed into the dispensing device 10. Memory 52 is configured to record information such as a time when the carousel 20 has been rotated, absolute time between two consecutive rotations, etc. In one embodiment, the memory comprises an Electrically Erasable Programmable Read-Only Memory (EEPROM).

In an example implementation, a motor control chip (not shown) is provided to appropriately power the motor 36. Further a real-time clock may also be provided to determine the appropriate time to lock/unlock the dispensing device 10.

In another example implementation, LED indicators (not shown) are also provided to indicate that the dispensing device 10 has to be rotated. LED indicators may also be used to confirm that the rotation has occurred. In one embodiment, an audio indicator is provided to indicate when it is time to advance the pill box. A connector (not shown) is provided to communicate data stored in the dispensing device 10 to external systems.

In an example implementation, a battery 58 is positioned as shown in FIG. 7 to power the dispensing device 10. In addition, battery protection circuitry (not shown) may be provided to prevent damage to the battery and battery charging circuitry may be provided to charge the battery. In one embodiment, tracking means 42 is disposed on the dispensing device 10 to determine a position of the rack gear

38. In an example implementation tracking means 42 may be a sensor which is used to detect a change in the battery to determine whether the motor 36 is still moving the rack gear 38. A change in the battery voltage indicates whether the motor 36 is moving the locking component 32, or is stalled due to the rack being at the end of its range of travel. If such a change is sensed, the motor 36 can be immediately turned off.

In one embodiment, an analog pin on a microcontroller (not shown) that references a fixed voltage is used to sense the battery voltage. It may be noted that the battery voltage may also be sensed externally using a resistor-divider and a Zener diode. For example, a change in the battery voltage occurs when the motor 36 transitions between an off state, an on and turning state, and an on and stalled state. Each of the three states can be detected. When the command is given to move the locking mechanism 32, the states will transition from the motor 36 in an off state to an on state to an on and stalled state. In some instances, the states may transition from a motor 36 in an off state to an on and stalled state.

In an example scenario, a user is provided a pill box 10 pre-loaded with prescription pills in the compartments 23. In this example scenario, a doctor has prescribed that the user take 1 pill, three times per day at intervals of every 8 hours. At 9 in the morning, the pill box 10 unlocks, lights and buzzers go off on the pill box 10 to alert the user, and the user advances the pill box 10 by turning the handle 16, which turns the carousel 20, which rotates until the locking component 32 is engaged. The user accesses a compartment, removes contained pills and takes the pills as prescribed. At 11 am, after 2 hours the user decides that they would like to take another pill well before the next prescribed time, which is about 5 pm (e.g. 8 hours after their first dose). The user attempts to rotate the carousel 20 in a clockwise manner to obtain the next pill, however referring to FIG. 4, state 3, the locking component 32 is in the rear position, preventing the carousel 20 from moving forward to the next compartment thereby preventing the user from prematurely accessing the next pill.

In another example scenario, it is now 5 pm. Referring to FIG. 4, State 4, the motor 36 moves, the locking component 32 slides into the forward position, and the pill box 10 is unlocked. The user can now advance the pill box 10 by one compartment by rotating the handle 16. Once that compartment is rotated, the user cannot rotate the handle, and thereby the carousel, backward or forward until the pill box is unlocked again.

Method to Prevent Unauthorized Access of Dispensing Devices

Embodiments described herein provide a dispensing device (e.g. a pill box) for dispensing medication. In various embodiments, the dispensing device may include a base member, a carousel coupled to the base member and configured to rotate about the base member. In some embodiments, the dispensing device may include one or more compartments formed within the carousel and configured to store a single dose of medication. In some embodiments, the dispensing device includes a lid configured to enclose the base and the carousel and a cover disposed on a top portion of the carousel.

Embodiments may include a securing mechanism disposed on the dispensing device configured to prevent unauthorized access to contents stored within the dispensing device. In some embodiments the securing mechanism includes a tamper detection device operatively coupled to the cover or the base member and configured to generate an alarm signal in response to displacement of the cover. Embodiments may include a linking component coupled to the tamper detection device in a manner so that when the tamper detection device generates the alarm signal when the linking component is decoupled from the tamper detection device. In some embodiments the linking component may include an electronic device or a mechanical component.

The dispensing device may be utilized for storing medication such as but not limited to pills, capsules, ampules, dose-packs, vials, vitamins, gels, injectables and creams. However, the dispensing device may also be used to store pet food, snacks (e.g., candy or gum), nutritional supplements, patches (e.g., nicotine or birth control), sublingual strips, prizes (e.g., stickers or marbles), reminder messages (e.g., hand-written notes), instructions for a scavenger hunt or daily operation of machinery, encrypted codes for logging in each day, etc. The dispensing device may be mounted on a wall for tracking when the handle is rotated, (and then possibly unlocking a door with this information).

Referring to FIGS. 1 and 2, an example embodiment of a dispensing device 10 is illustrated. The dispensing device 10 includes a base member 12, a lid 14, a handle 16 disposed over the lid 14 and a cover 18 disposed over the handle. The dispensing device 10 includes a carousel 20 that is configured to rotate at the base member 12. The articles stored in the dispensing device 10 can be accessed through a window 19.

The base member 12 is coupled to a carousel 20 at the center of the base member 12. In one embodiment, the base member 12 comprises a spindle 13 that is operatively coupled to a shaft 28 of the carousel 20 and configured to facilitate rotation of the carousel 20. The carousel 20 further includes a plurality of fins 22 coupled to the shaft 28, each fin 22 extending outwards from the shaft 28 to form a curved wall. The compartments 23 are formed by an area formed between two consecutive fins 22 and a portion of the inner wall of the base member 12.

In some implementations, the compartments 23 may be formed by self-contained units instead of being defined by the walls of the carousel. In some implementations these self-contained units may be bundt pan shaped. In other implementations the compartments 23 may be formed from fins that extend from the base member 12 to the shaft.

Referring again to FIGS. 1, 2, and 8, a cover 18 is on a top portion of the handle 16. In the illustrated embodiment, the cover is fastened to the base 12 using the screws 226 and the standoffs 242. In one embodiment, the window 19 is as wide as one compartment 23. Referring to FIGS. 2-3, in some implementations, an annular snap 238 is disposed around the circumference of the dispensing device. The snap 238 facilitates locking the lid 14 to the base 12.

Figure 8:
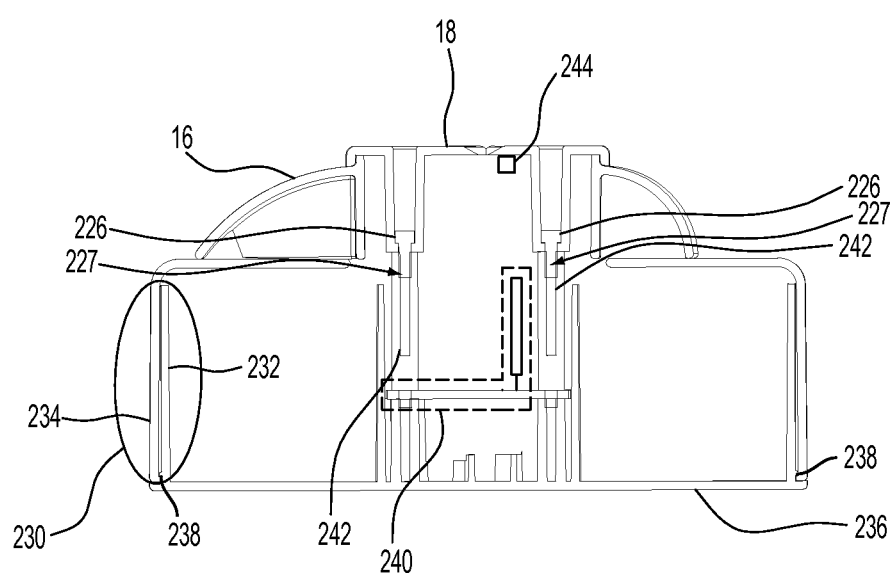
FIG. 8 is cross-sectional view of an example embodiment of a dispensing device.

The dispensing device includes a securing mechanism to prevent unauthorized access to contents stored within the dispensing device. FIG. 8 is a cross-sectional view of an example dispensing device implemented according to aspects of the present technique. The dispensing device comprises a securing mechanism configured to prevent unauthorized access to contents stored within. The securing mechanism includes a security component, a tamper detection device and security fasteners.

Referring again to FIG. 8, the securing mechanism 230 is formed by an inner wall 232 extending upwards from a base plate 236 of the base member 12 and an outer wall 234 of the lid 14. The outer wall 234 of the lid 14 and the inner wall 232 of the base 12 overlap the full height of the carousel, securing the contents inside the compartments and preventing the pieces from being pried apart. The thickness of the inner wall 232 and outer wall 234 is designed to maximize strength while reducing overall weight. In one embodiment, the thickness of the inner wall 232 is about 1.5 mm and the thickness of the outer wall 234 is about 1.5 mm.

The securing mechanism 230 may include at least one security fastener 227. In some implementations the security fastener 227 is a single screw that extends from the cover 18 to the base 12. In other implementations the security fastener 227 includes screws 226 and standoffs 242 configured to mechanically fasten the cover 18 to the base 12. The security fastener 227 requires a special tool, not readily found in most homes or stores, to remove it from the base 12 member. Thus, in an example implementation all parts of the assembly are sandwiched between the cover 18 and the base 12 making it difficult to remove an intermediary part without disconnecting the cover 18 and the base 12. In one implementation, the security fastener 227 is a screw fastener. Non-limiting example sizes and dimensions for the screws 226 include 2-56 Torx-head steel screws, ¼" long. Non-limiting examples of the standoffs 242 are 2-56 male-female standoffs. In some implementations the security fastener could be screws with other head styles, such as tri-lobe, or could be snaps integrated into the lid that require a custom tool to disengage.

Referring to FIG. 8, in an embodiment the securing mechanism 230 includes a tamper detection device 240 operatively coupled to the cover or the base member and configured to generate an alarm signal in response to displacement of the cover. The tamper detection device 240 works in conjunction with a linking component 244 and is configured to generate the alarm signal when the linking component 244 is decoupled from the tamper detection device. In one embodiment, the linking component 244 is fastened to the cover 18, and indicates when the cover has been removed from the pill box.

Figure 9:
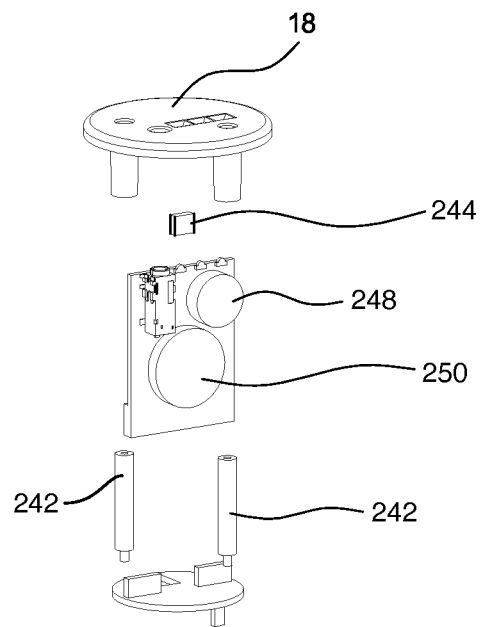
FIG. 9 is an exploded view of an example securing mechanism disposed within a dispensing device.
Figure 9:
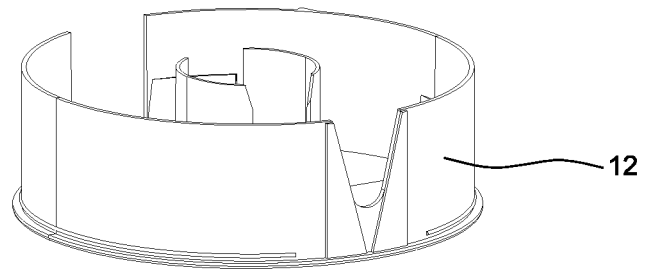
Figure 10:
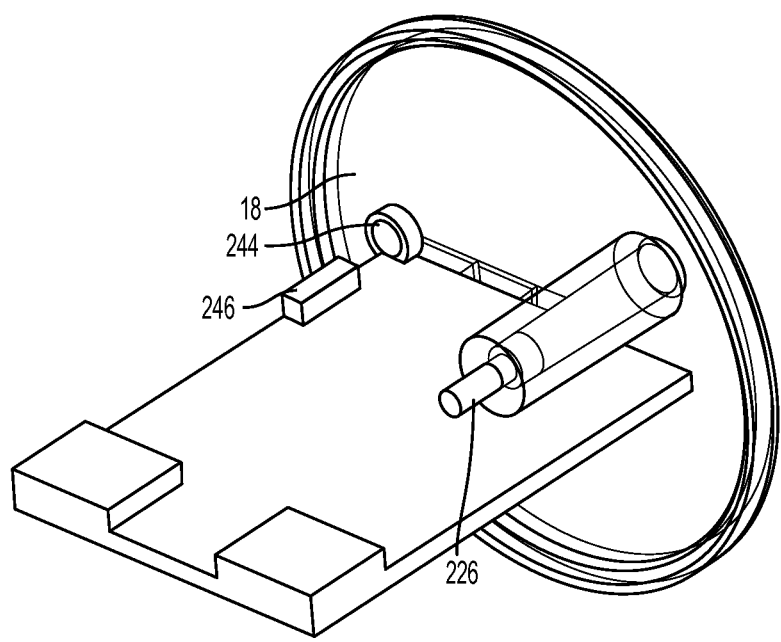
FIG. 10 is a partial perspective view of a portion of the securing mechanism of FIG. 9.

Referring to FIGS. 9 and 10, the tamper detection device includes a sensor 246 processing circuitry 248 and alarm generator 250. The linking component 244 can be positioned on an underside of the cover 18. The linking component is electronically or mechanically coupled to the sensor 246. The sensor 246 detects a displacement of the cover 18. In an example implementation, the sensor 246 is a magnetic reed switch and the linking component 244 is a magnet. In an example scenario, the reed switch is in one state when the magnet (affixed to the cover 18) is close by, and is in another state when the magnetic field is removed. Processing circuitry 248 is disposed on the base member 12 and is also configured to receive signals from the sensor 246.

Figure 11:
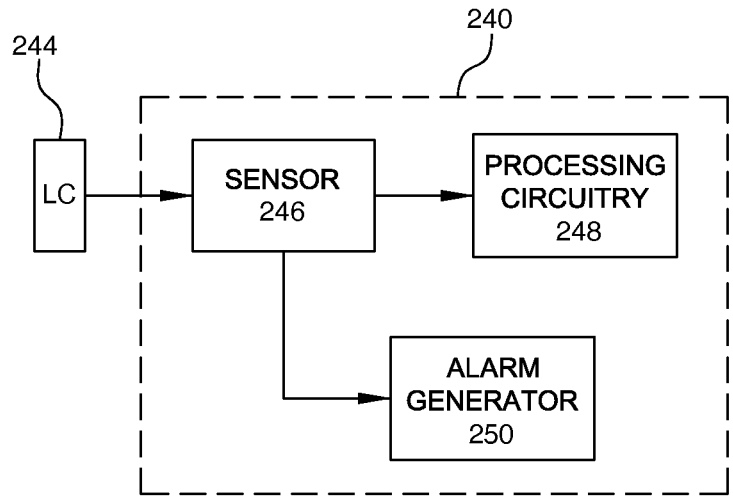
FIG. 11 is a diagrammatic view of an example embodiment of a tamper detection device used in a dispensing device.

FIG. 11 illustrates an example simplified block diagram of an example tamper detection device 240 which may be used to implement the embodiments described herein. In some implementations, the tamper detection device 240 and the linking component 244 are disposed adjacent to each other. In one embodiment, the linking component 244 is disposed on an underside of the cover 18 and the tamper detection device 240 is disposed on the base of the dispensing device. However, it may be noted that the position of the tamper detection device 240 can be interchanged with the position of the linking component 244.

In some implementations, the linking component 244 is a magnet. In one embodiment, the linking component 244 comprises an electronic device or a mechanical component. Examples of electronic devices include magnets, optical emitters/detectors, conductive material interfacing with other conductive material (closing a switch), or non conductive material blocking, electronic plugs/shunts/header pin, and the like. Examples of mechanical components include mechanical couplers, contact switches and the like.

The linking component 244 may be electronically or mechanically coupled to the tamper detection device 240. The tamper detection device includes a sensor 246, processing circuitry 248 and alarm generator 250.

In an example embodiment, the sensor 246 is a magnetic sensor. In an example scenario when the cover 18 is secured to the dispensing device 10, the magnet 244 generates an electromagnetic field. However, when the cover 18 is displaced from its original position, the electromagnetic field generated by the magnet 244 is altered. The tamper detection device 240 is configured to detect the change in electromagnetic field. When the tamper detection device senses such a change, the alarm generator 248 generates an alarm signal. Example alarm signals include an audible tone that can be selected for duration, volume, style, etc. In one embodiment, the alarm generator may include light emitting diodes that are enabled when a change is detected.

In some implementations, the tamper detection device includes processing circuitry 248 disposed within the dispensing device and configured to record a time at which the linking component 244 is decoupled from the tamper detection device 240. The processing circuitry may include a memory device that is configured to store a time log that contains such as time and date at which such changes were detected, time and date at which the carousel 20 was rotated, and the like. In one embodiment, the processing circuitry is configured to transmit the time log to a central computing device, such as a server. Further, the processing circuitry may be configured to transmit the time log in real time and/or wirelessly.

The above described features of the dispensing device 10 can be implemented in a pill box that is adapted to store medication within its compartments. An advantage of the embodiments described herein is that they may prevent a user from tampering with medication stored inside the pill box.

Figure 12:
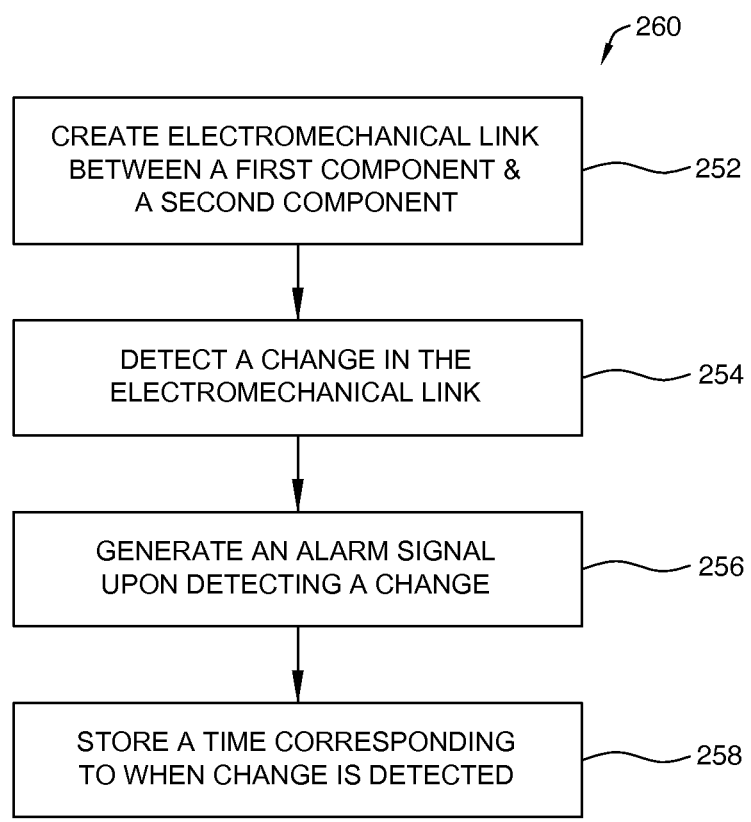
FIG. 12 is a flow chart describing an example method by which unauthorized access to a dispensing device is detected.

FIG. 12 illustrates a simplified flow diagram for a method for detecting unauthorized access to a pill box. The pill box may include several components and may contain several compartments in which the medication is stored. In an example embodiment, an example pill box similar to the embodiments of the dispensing device 10 described above, with reference to FIGS. 8-11, may be used to implement the method described with reference to FIG. 12. However, it should be understood that the technique described below can be implemented in other types and designs of pill boxes and dispensing devices.

At step 252, an electromechanical link is created between a first component and a second component of the pill box. In one embodiment, the electromechanical link is created by using a magnet that generates an electromagnetic field. In another embodiment, the electromechanical link is created by using an optical emitter that creates an optical path. In some embodiments, the electromechanical link is created by using a mechanical switch. In one embodiment, the first component is a lid of the pill box and the second component is a base of the pill box.

At step 254, a change in the electromechanical link is detected. The change is indicative of a displacement of the first component with respect to the second component from their respective initial positions. The change is detected using a sensor, non-limiting examples of which include electronic sensors, magnetic sensors, optical sensors, and the like.

At step 256, an alarm signal is generated in response to the change detected in the electromechanical link. The alarm signal can be an acoustic indicator signal and/or an optical indicator signal. The alarm signal may be generated by an alarm signal generator such as light emitting diodes disposed on an outside of the pill box or by an audio device that generates an audio signal.

At step 258, a time at which the change in electromechanical link is detected is stored using a memory device. It may be noted that the memory device can also record other activities, examples include but are not limited to the time at which a compartment is accessed, time at which the pill box was filled, automatic alarm times, and the like. Such activities are collectively referred to as a time log and are stored in the memory device. Further the time log is transferred to a computing device for appropriate analysis. For example, the time log may be transferred via a server. Example computing devices include a tablet, a mobile internet device, a cell phone, laptop, desktop or other computer.

The above described techniques have several advantages including providing a robust design for a dispensing device 10 that cannot be easily broken or damaged. Further, the tamper detection feature may help detect tampering by unauthorized persons. The dispensing device 10 also includes data storage and transmission capabilities that enable a person monitoring the dispensing device to obtain accurate information about the state of the device.

In an example implementation, the dispensing device 10 is built from a material that is impact-resistant and environment-tolerant. An advantage of such a material is that it makes the device more robust and resistant to tampering and breakage. Non-limiting examples of material that can be used to form the dispensing device include Acrylonitrile butadiene styrene (ABS), polycarbonate, acetyl, polypropylene, polyethylene, polyvinyl chloride (PVC), aluminum, steel, or other material, including blends of the above or including filler material such as glass or carbon fiber to alter the material properties.

Central Monitoring for a Healthcare Network

Example embodiments are generally directed to central monitoring systems used to monitor medication systems. The following description is with reference to a pill box used for dispensing medicines, however it should be understood that the techniques described herein may be applied in any type of medication storage device that is used to dispense articles stored within in a controlled manner.

Figure 13:
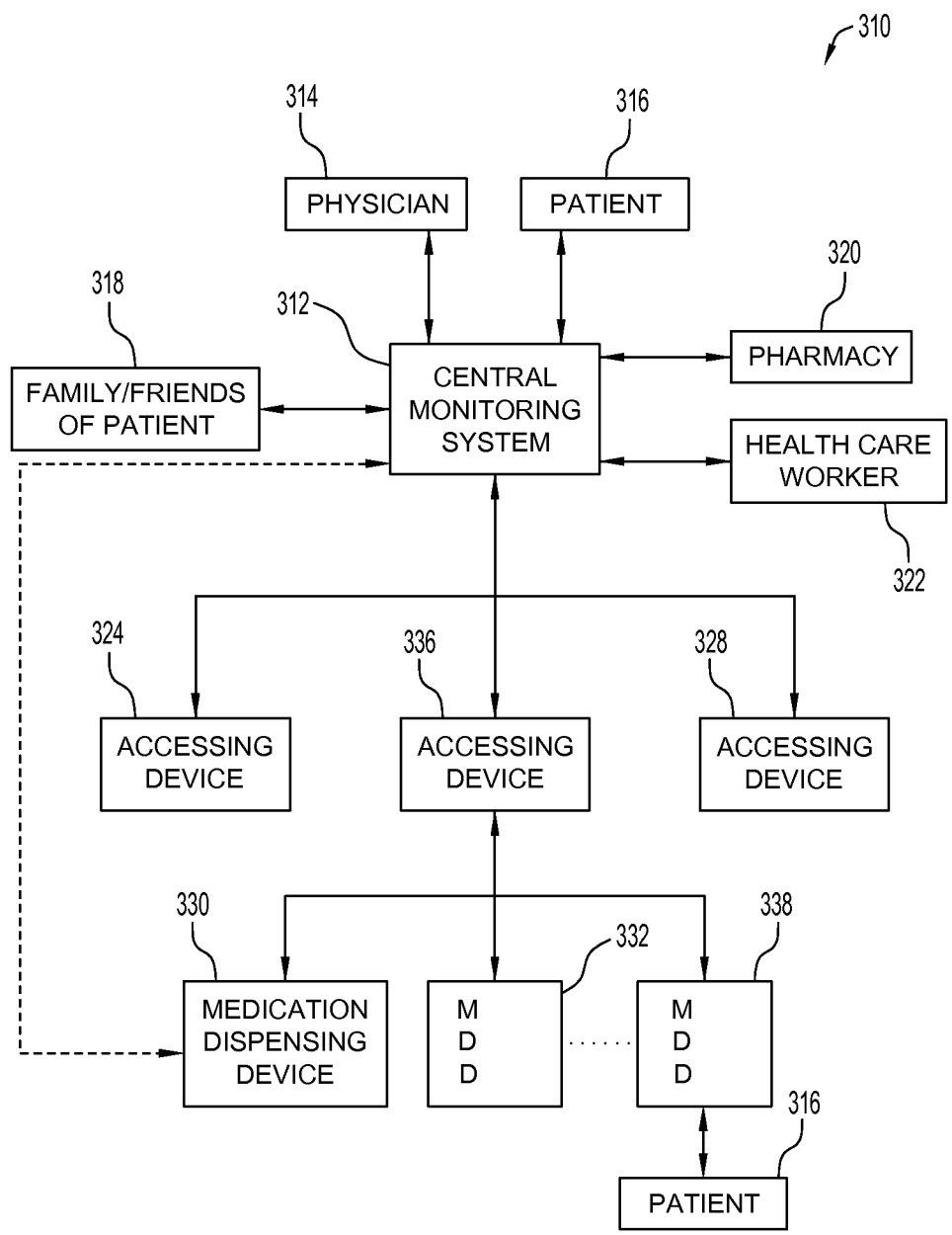
FIG. 13 is an example of a healthcare environment in accordance with at least one embodiment.

FIG. 13 is an example embodiment of a healthcare environment. The healthcare environment 310 includes a computing device 312 (e.g., a central monitoring system) configured to monitor dispensing devices, medication dispensing devices or MDDs 330, 332 and 338. The computing device 312 is coupled to various entities such as a physician 314, patient 316, family and/or friends 318, pharmacy 320 and healthcare worker 322. The computing device 312 is also in communication with accessing devices 324, 336 and 328. As can be seen in FIG. 13, each accessing device 324, 336 and 328 is associated with one or more medication dispensing devices 330, 332, and 338. The accessing devices 324, 336, and 328, the computing device 312 and the medication dispensing devices 330, 332, and 338 together form a central monitoring system.

For ease of description when referring to a single accessing device, accessing device 336 will be referenced or when referring to a single dispensing device, dispensing device 338 will be referenced. It is to be understood that embodiments and implementations are not limited to these single devices and could be any one or more of the other devices disclosed and shown herein.

Accessing devices 324, 336 and 328 are configured to provide access to a fixed or variable number of medication dispensing devices. For example, the accessing device 336 is configured to access medication dispensing devices 330, 332 and 338. Similarly, accessing devices 324 and 328 may be configured to access dispensing devices 330, 332, and 338 or may be configured to access a set of medication dispensing devices (not shown). Each accessing device may be electronically and/or mechanically coupled to one or more medication dispensing devices.

An example accessing device 336 can be programmed with a unique identity tag. In one embodiment, the identity tag includes an alphanumeric code. When the accessing device 336 is coupled to a medication dispensing device 338, the identity tag is transferred to the medication dispensing device 338 and stored in an internal memory of the medication dispensing device 338. In one embodiment, the identity tag can be used to determine a device interaction status of the dispensing device 338. As used herein, device interaction status can be used to establish if any interaction has been initiated between a patient and another entity such as a patient supervisor.

In some embodiments, the accessing device 336 can be configured to receive device data transmitted by the medication dispensing device 338. Device data may include present or past device state information, and/or a snapshot of various parameters of the medication dispensing device 338. In some implementations, device data may include one or more of the following: the date and time at which the medication dispensing device was accessed by a patient and/or the accessing device, the number of articles present within the medication dispensing device, the number of reminders that have been set, a time until next reminder, a lock state, a tamper state, an ambient temperature, and a battery voltage, etc.

In some implementations, device data includes a historical record of time-stamped events. For example, device data may include when articles have been dispensed, past interactions with accessing devices, past recharges and resets of the device, etc. In some implementations, device data includes prescription data such as size, quantity, brand and type of medication being taken.

The computing device 312 is further configured to communicate with the medication dispensing device 338. In one embodiment, the medication dispensing device 338 is configured to communicate wirelessly with the central monitoring system (e.g., computing device 312). In some embodiments, the medication dispensing device 338 is configured to communicate with the computing device 312 using a wired connection (not shown) or via another computing device.

The computing device 312, when coupled to the medication dispensing device 338, is configured to receive the identity tag provided by the accessing device 336. Further the central monitoring system 312 is configured to process the identity tag to determine the device interaction status of the dispensing device 336 within the healthcare network.

The device interaction status may then be relayed to the various entities that are coupled to the computing device 312 via a communication module (not shown) implemented in the central monitoring system 312. The computing device is also configured to transmit alerts to one or more secondary central monitoring systems associated with one or more medication dispensing devices that are being monitored by the computing device. Examples of secondary central monitoring systems include personal computer systems belonging to the patient or patient's family, hand held devices such as mobile phones, PDAs, etc.

Figure 14:
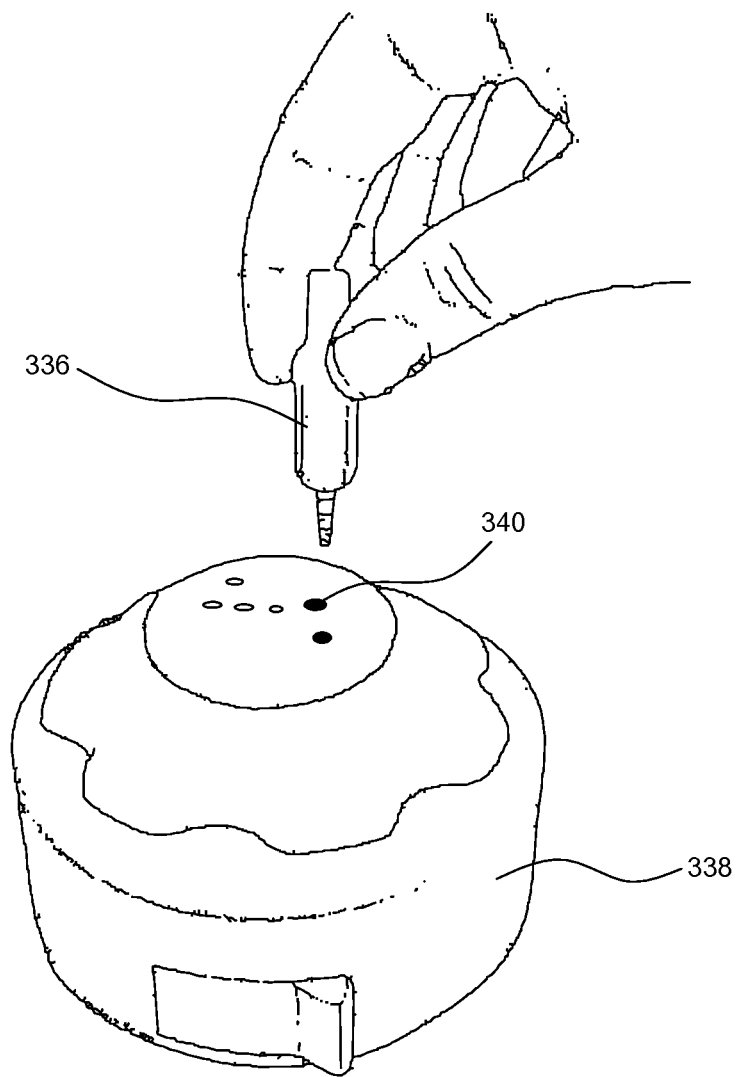
FIG. 14 is an example accessing device for a medication dispensing device in accordance with at least one embodiment.

Referring to FIG. 2 and FIG. 14, illustrated is an example embodiment of a medication dispensing device 10. The dispensing device described below may be utilized for storing medication such as but not limited to pills, capsules, ampules, dose-packs, vials, vitamins, gels, injectables, and creams. The medication dispensing device 10 includes a base member 12, a lid 14 and a handle 16 disposed over the lid 14.

In the illustrated embodiment, the dispensing device 10 includes compartments (not shown) within which articles are stored. By rotating the handle 16, each compartment may be accessed through window 19. Further, a cover 18 is disposed over the handle to prevent the contents of the dispensing device 10 from being tampered. Authorized personnel (e.g. a healthcare provider or patient) may open the dispensing device 10 by coupling an accessing device 336 to the cover 18. In some implementations, the dispensing device 10 may automatically be opened without the accessing device, for example the dispensing device 10 can be configured to open only at a predetermined time.

Referring to FIG. 14, an example embodiment of an accessing device 336 may be coupled to a medication dispensing device 338 through interface 340 as shown. As can be seen in the illustrated example, the interface 340 may be disposed on the cover 18 of the medication dispensing device 338. The interface 340 may be wired or wireless. For example, the wired interface may communicate via RS-232 communication or USB, and the wireless interface may be Bluetooth, Zigbee, Wi-Fi, etc.

In the illustrated embodiment, the accessing device 336 is physically inserted into the interface 340. However, the accessing device 336 may also interact with the interface without physical contact, for example using infrared sensors or radio frequency sensors. In one embodiment, the accessing device 336 is a biometric reader that can be electronically coupled to the medication dispensing device 338. In some implementations, the accessing device is a 4-conductor stereo jack with internal electronics that can transmit and receive data, as well as share power and ground.

Figure 15:
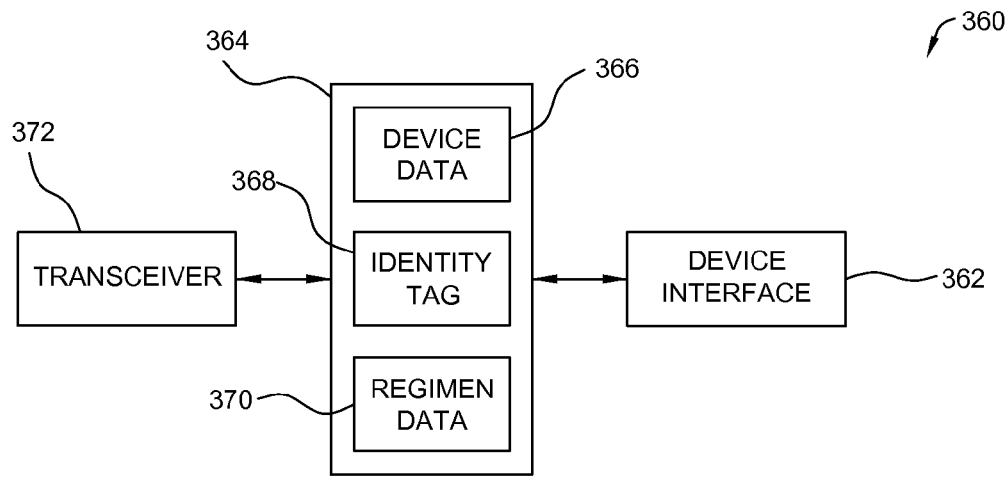
FIG. 15 is a block diagram of an accessing device in accordance with at least one embodiment.

FIG. 15 is a block diagram illustrating an example embodiment of an accessing device 360. The accessing device 360 comprises a transceiver 372, memory circuitry 364 and device interface 362.

Device interface 362 is configured to allow the accessing device to interact with an associated medication dispensing device 338. In one embodiment, the device interface 362 is a mechanical key that can be inserted into the medication dispensing device 338. In another embodiment, the device interface 362 is a sensor that is configured to lock or unlock the medication dispensing device 338.

Memory circuitry 364 is configured to store the accessing device's 360 identity tag 368 and uniquely identifies a particular accessing device. In one embodiment, the identity tag 368 comprises an alphanumeric code. Specific identity tags can cause particular behaviors in particular medication dispensing devices 338. For example, identity tags 368 can be used to unlock the medication dispensing device 338 for access to the next compartment, for putting the device into a refill-state in which it is always unlocked, or as a security feature which is required to be present to unlock the medication dispensing device 338. Memory circuitry 364 is further configured to store device data 366 and/or regimen data 370 of one or more medication dispensing devices 338.

In an embodiment, transceiver 372 is configured to transmit the identity tag of the accessing device 360 when it is coupled to the medication dispensing device 338. In some implementations, the accessing device 360 is configured to receive data such as device data from the dispensing device 338. The accessing device is also configured to receive regimen data from the central monitoring system 312. The identity tags, device data and regimen data can be further analyzed to monitor a patient associated with each dispensing device 338. The manner in which the central monitoring system 312 analyses the data is described below in further detail.

Figure 16:
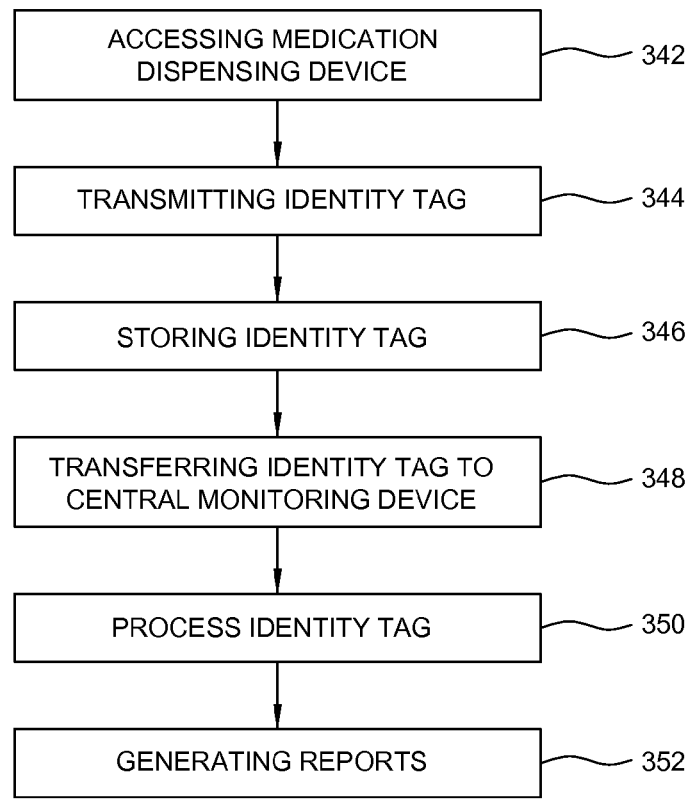
FIG. 16 is a flow chart illustrating one technique by which a central monitoring system monitors a healthcare network in accordance with at least one embodiment.

FIG. 16 is a flow chart illustrating one method by which a central monitoring system monitors an interaction between a dispensing device 338 and a healthcare supervisor. The dispensing device 338 operates with an accessing device 336, which is used to transmit and receive information associated with the dispensing device 338.

At step 342, a medication dispensing device 338 distributed within a healthcare network is accessed. In one embodiment, a healthcare supervisor accesses the medication dispensing device. In some implementations, the healthcare network can employ several healthcare supervisors. Each supervisor is provided with an accessing device 336. It may be also noted that a single accessing device 336 may be used to access more than one medication dispensing device 338. In one embodiment, the accessing device 336 is mechanically or electronically coupled to the medication dispensing device 338 in order to access data.

At step 344, an identity tag is transmitted by the accessing device 336 to the medication dispensing device 338 it has been coupled with. In one embodiment, the identity tag is an alphanumeric code.

At step 346, the identity tag is stored in the medication dispensing device 338.

At step 348, the identity tag is transmitted to the computing device. In one embodiment, the identity tag is transmitted wirelessly to the central monitoring system. In another embodiment, the identity tag is transmitted when the dispensing device is coupled to a computing device. In some implementations, a time stamp of the time of coupling is transmitted to the computing device.

At step 350, the computing device processes the identity tags received from dispensing devices 330, 332, and 338 in the healthcare network. The identity tags are processed to determine whether a healthcare worker has made a visit to a patient and the corresponding time at which the visit was made. In some implementations, the computing device 312 processes data such as state and history information received from the dispensing device 338.

At step 352, the computing device can create reports about healthworker-patient interactions as well as times of use and access of the medication dispensing devices.

Figure 17:
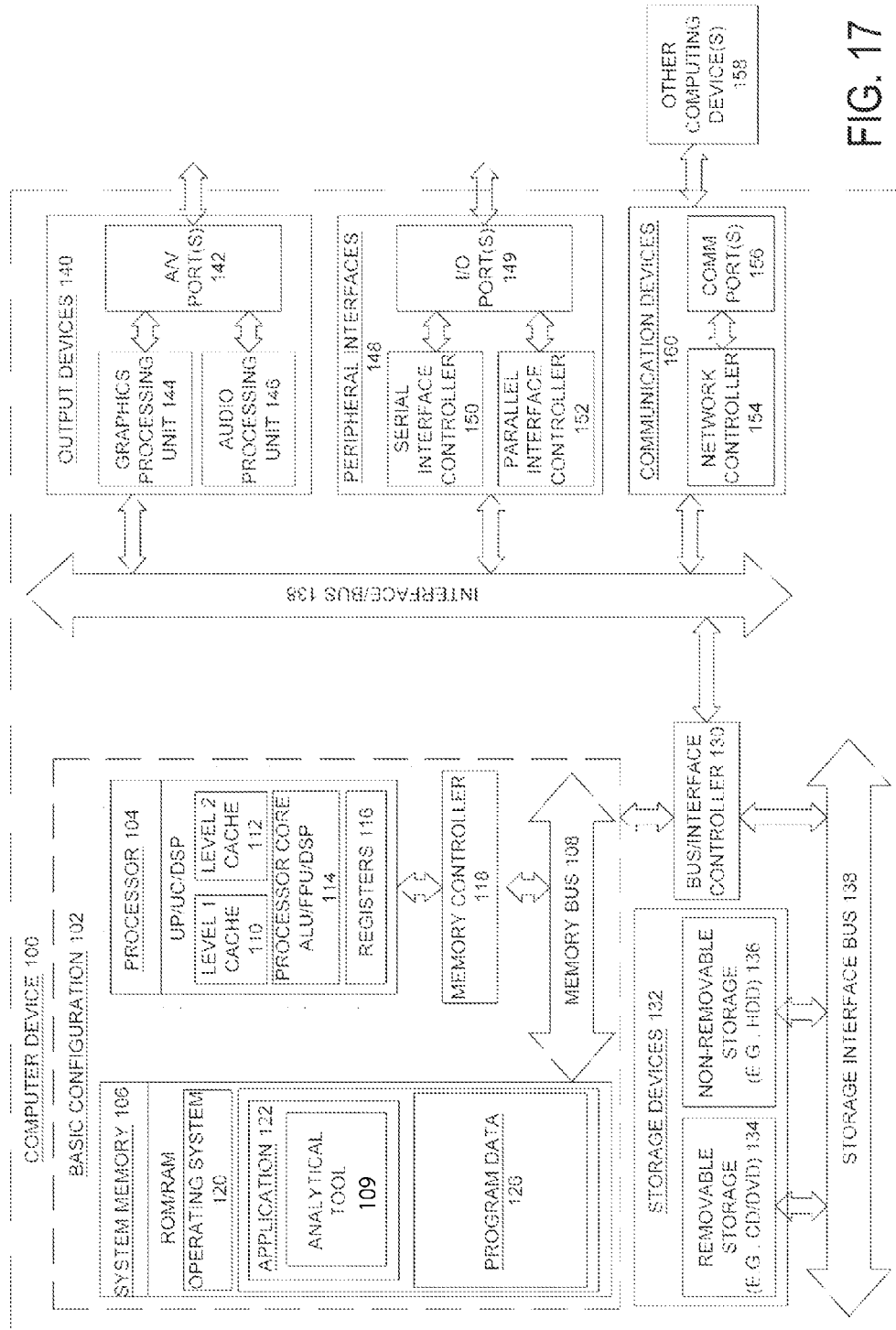
FIG. 17 is a block diagram of an example central monitoring system in accordance with at least one embodiment.

FIG. 17 is a block diagram illustrating an example embodiment of a central monitoring system 312. In the illustrated FIG. 17, the central monitoring system 312 is shown as "computer device" 100. In an embodiment, computer device or central monitoring system 100 is configured to monitor several medication dispensing devices distributed within a healthcare network. In an example configuration 102, central monitoring system 100 includes one or more processors 104 and a system memory 106. A memory bus 108 may be used for communicating between processor 104 and system memory 106.

Depending on the desired configuration, processor 104 may be of any type including but not limited to a microprocessor ($\mu P$), a microcontroller ($\mu C$), a digital signal processor (DSP), or any combination thereof. Processor 104 may include one or more levels of caching, such as a level one cache 110 and a level two cache 112, a processor core 114, and registers 116. An example processor core 114 may include an arithmetic logic unit (ALU), a floating-point unit (FPU), a digital signal processing core (DSP Core), or any combination thereof. An example memory controller 118 may also be used with processor 104, or in some implementations memory controller 118 may be an internal part of processor 104.

Depending on the desired configuration, system memory 106 may be of any type including but not limited to volatile memory (such as RAM), non-volatile memory (such as ROM, flash memory, etc.) or any combination thereof. System memory 106 may include an operating system 120, one or more applications 122, and program data 126. Application 122 includes an analysis module 109 that is arranged to insert one or more services in the software application. Program data 126 may include data related to one or more dispensing devices such as identity tags, device data and/or regimen data, and history of device data. In some embodiments, application 122 may be arranged to operate with program data 126 on operating system 120 such that interaction between the dispensing devices and external entities are monitored. This described basic configuration 102 is illustrated in FIG. 17 by those components within the inner dashed line.

Central monitoring system 100 may have additional features or functionality, and additional interfaces to facilitate communications between basic configuration 102 and any required devices and interfaces. For example, a bus/interface controller 130 may be used to facilitate communications between basic configuration 102 and one or more data storage devices 132 via a storage interface bus 138. Data storage devices 132 may be removable storage devices 134, non-removable storage devices 136, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 106, removable storage devices 134 and non-removable storage devices 136 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by central monitoring system 100. Any such computer storage media may be part of central monitoring system 100.

Central monitoring system 100 may also include an interface bus 138 for facilitating communication from various interface devices (e.g., output devices 140, peripheral interfaces 148, and communication devices 160) to basic configuration 102 via bus/interface controller 130. Example output devices 140 include a graphics processing unit 144 and an audio processing unit 146, which may be configured to communicate to various external devices such as a display or speakers via one or more A/V ports 142. Example peripheral interfaces 148 include a serial interface controller 150 or a parallel interface controller 152, which may be configured to communicate with external devices such as input devices (e.g., keyboard, mouse, pen, voice input device, touch input device, etc.) or other peripheral devices (e.g., printer, scanner, etc.) via one or more I/O ports 149. An example communication device 160 includes a network controller 154, which may be arranged to facilitate communications with one or more other central monitoring systems 158 over a network communication link via one or more communication ports 156.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Central monitoring system 100 may be implemented as a portion of a small form factor portable (or mobile) electronic device such as a cell phone, a personal data assistant (PDA), a personal media player device, a device worn on the body, a personal headset device, wearable computer, an application specific device, or a hybrid device that includes any of the above functions. Central monitoring system 100 may also be implemented as a personal computer including both laptop computer and non-laptop computer configurations. The central monitoring device is configured to generate various reports related to the dispensing devices 330, 332, and 338 in the healthcare network. Some example user interface screens are described below with reference to FIG. 18 through FIG. 22.

Figure 18:
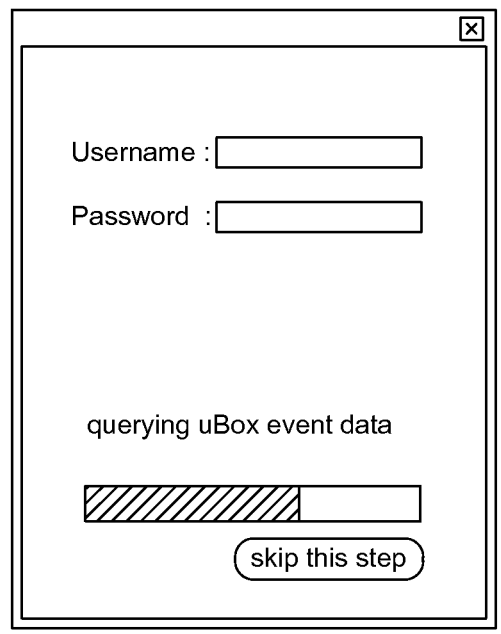
FIGS. 18 through 21 are example user interface screens generated by a central monitoring system in accordance with at least one embodiment.

FIG. 18 is an example login screen of a user interface implemented according to aspects of the present technique. The screen includes areas where a user can input his/her user name and password. The login screen also includes an event data query status bar and a button to skip the event data querying. Upon authentication of the user name and password, the user interface displays user details as shown in FIG. 19.

Figure 19:
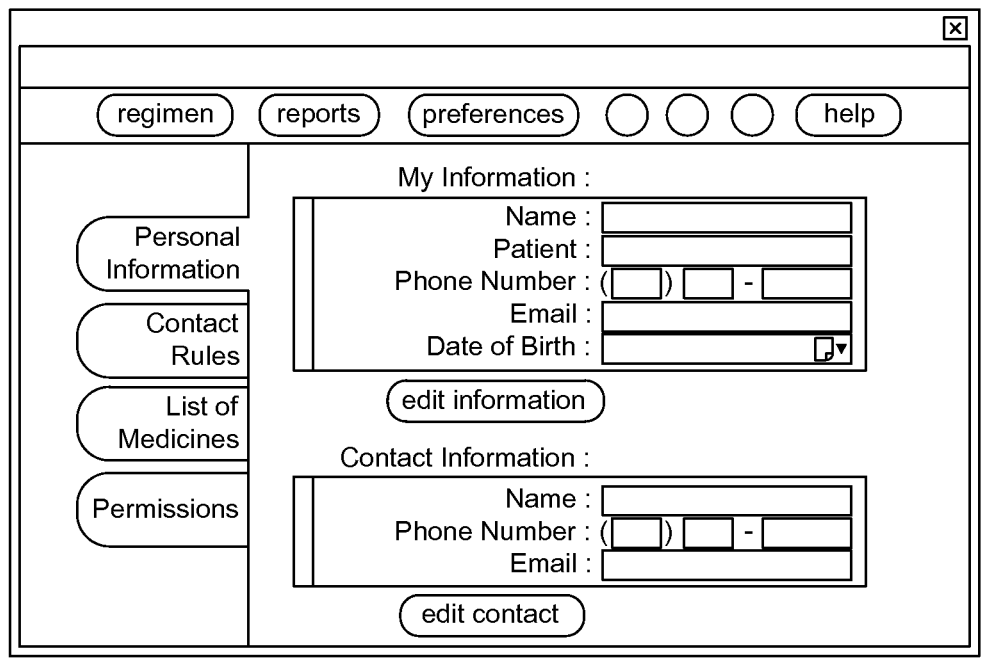
Figure 20:
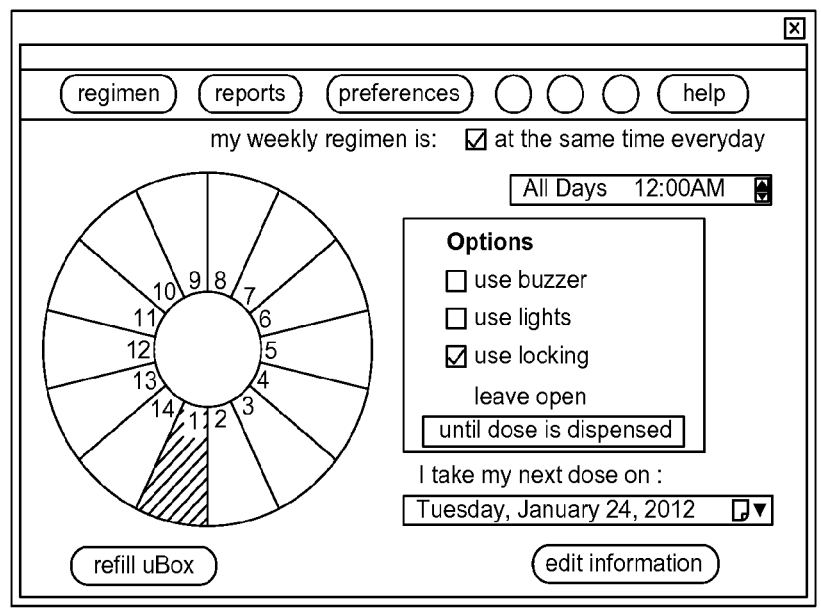

The user interface screen shown in FIG. 19 comprises three tabs associated with a user's regimen, reports and preferences, respectively. The illustrated screen displays personal details of the user (e.g., name, patient ID, phone number, email date of birth) and contact information. The screen can also display contact rules (e.g., how and when a patient prefers to be contacted and/or with whom the healthcare provider is authorized to communicate). The screen can show a list of medications currently prescribed to the patient and permissions that have been established for communicating with and/or treating the patient. The regimen tab is clicked to obtain information about a regimen of the user as shown in FIG. 20.

The user's regimen can be stored within the dispensing device. In an example implementation, regimen data may include one or more of the following: dosing schedule, medication names and physical descriptions. In some implementations, the regimen data is programmed into the dispensing device by a healthcare supervisor. In one embodiment, the data is programmed via a web application or local software on a computer. It can be downloaded to the dispensing device in either a wired or wireless manner.

The dosing schedule is used to set the reminder times. In one embodiment, a member of the healthcare circle such as a healthcare supervisor or family may opt to receive real-time notifications, either affirmative, such as being notified every time a dose is dispensed, or negative, such as only when a dose is missed by a certain time threshold. Further, a notification may be sent when a refill is due. A healthcare supervisor may also log in to the central monitoring system via a webpage or smart phone application to view adherence over time or other pertinent messages.

In another embodiment, the dispensing device is paired to another device, such as a smart phone, via wireless technology such as Bluetooth. In this example, when the pairing is disconnected, such as when the smart phone is physically too far away from the dispensing device to maintain a connection, an alert will be generated on the smart phone indicating a connection may be lost to the dispensing device.

Figure 21:
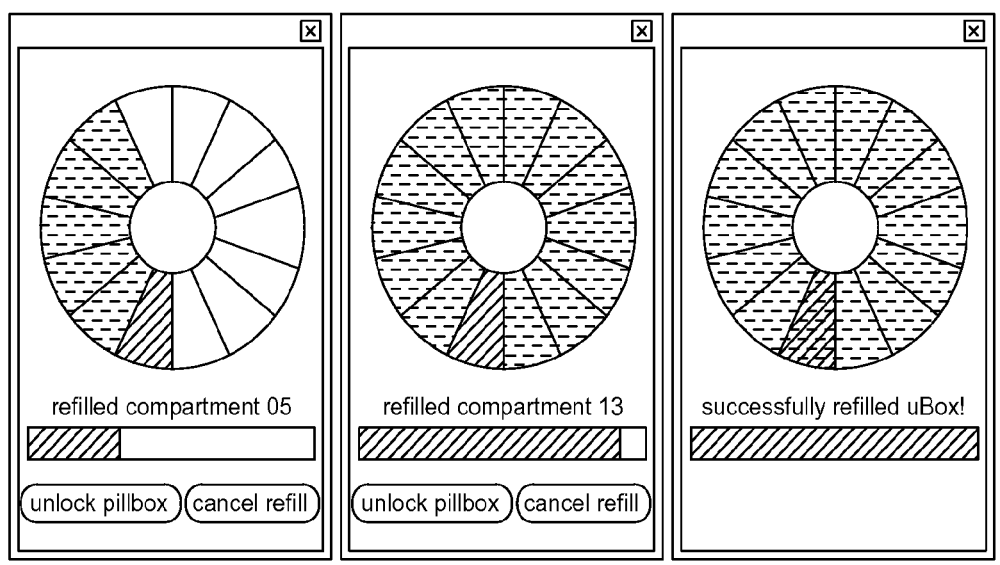

In a step, the dispensing device 338 is filled with the proper medication. The filled dispensing device 338 is then compared visually to the representation generated by the software for confirmation of proper loading as shown in FIG. 21.

Figure 22:
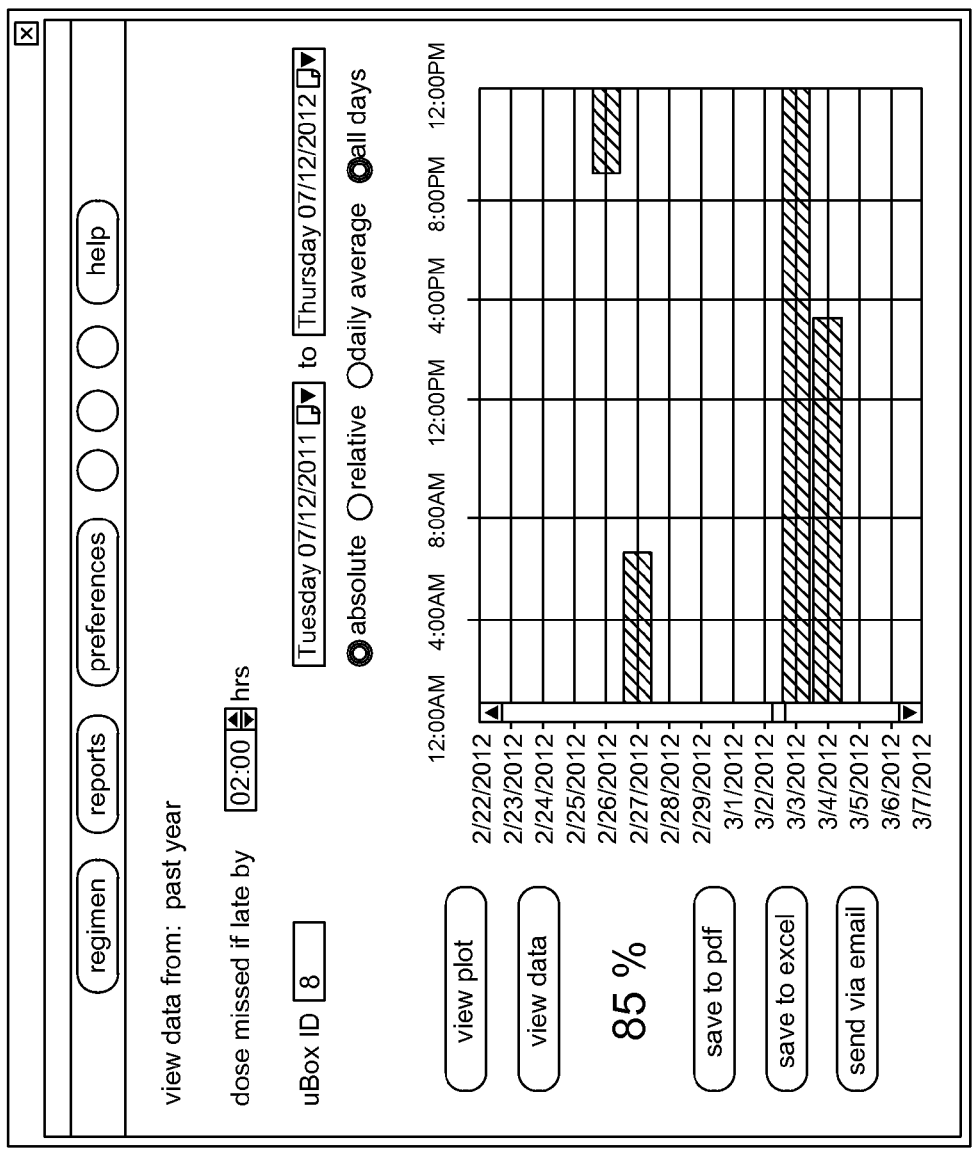
FIG. 22 is an example illustration of a displayed output reporting adherence scores for an example scenario.

FIG. 22 is an example illustration of a displayed output reporting adherence scores. The example shown indicates an adherence score of (85%), and when doses were supposed to have been taken and when they actually were taken (e.g. the shaded bars going across the screen). In an example implementation, the adherence score is calculated based on whether a dose was considered missed if taken late by a configurable time (e.g. if late by 2 hours). In some implementations, the date range for the report is also programmable. The data can be displayed as absolute times (e.g. dose meant to be taken at 9 pm on Feb. 26, 2012, but not taken until 6:30 am Feb. 27, 2012).

FIG. 23 is an example of a displayed output of a time-log of interactions between an accessing device (11392) and medication dispensing devices, as well as an example time-log of interactions between a medication dispensing device (89393) and accessing devices. In an example scenario, a healthcare worker carries around a unique accessing device (11392) and visits with various patients (and accesses their medication dispensing devices) on a regular basis. In another example scenario, a patient with a medication dispensing device (89393) is visited by two different healthcare workers (one carrying accessing device 11392 and one carrying accessing device 8923) at different times.

Dispensing Detection System and Method

Embodiments described herein provide a dispensing device (e.g., a pill box) for dispensing medication. In various embodiments, the dispensing device may include a base member, and a carousel coupled to the base member and configured to rotate about the base member. In some embodiments, the dispensing device may include one or more compartments formed within the carousel and configured to store a single dose of medication. In some embodiments, the dispensing device includes a lid configured to enclose the base and the carousel.

Embodiments described herein include a detection system using sensors to determine dispensation. In one embodiment, the system includes sensors disposed within the dispensing device and configured to generate a signal corresponding to a displacement of the carousel with respect to the base member. The system uses processing circuitry configured to receive the signal generated and record a time at which the signal was received.

The dispensing device may be utilized for storing medication such as but not limited to pills, capsules, ampules, dose-packs, vials, vitamins, gels, injectables, and creams. However, the dispensing device may also be used to store pet food, snacks (e.g., candy or gum), nutritional supplements, patches (e.g., nicotine or birth control), sublingual strips, prizes (e.g., stickers or marbles), reminder messages (e.g., hand-written notes), instructions for a scavenger hunt or daily operation of machinery, encrypted codes for logging in each day, and the like. The dispensing device may be handheld or mounted on a wall for tracking when the handle is rotated, (and then possibly unlocking a door with this information).

Referring to FIGS. 1 and 2, an example embodiment of a dispensing device 10 is illustrated. The dispensing device 10 includes a base member 12, a lid 14, a handle 16 disposed over the lid 14, and a cover 18 disposed over the handle 16. The dispensing device 10 includes a carousel 20 that is configured to rotate about the base member 12. The articles stored in the dispensing device 10 can be accessed through a window 19.

FIG. 2 is an exploded view of an embodiment of the dispensing device 10. The base member 12 is coupled to a carousel 20 at the center of the base member 12. In one embodiment, the base member 12 comprises a spindle 13 that is operatively coupled to a shaft 28 of the carousel 20 and configured to facilitate rotation of the carousel 20. The carousel 20 further includes a plurality of fins 22 coupled to the shaft 28, each fin 22 extending outwards from the shaft 28 to form a curved wall. The compartments 23 are formed between two consecutive fins 22 and a portion of the inner wall of the base member 12.

In some implementations, the compartments 23 may be formed by self-contained units (not shown) instead of being defined by the walls of the carousel 20. In some implementations these self-contained units may be bundt pan shaped. In other implementations the compartments 23 may be formed from fins that extend from the base member 12 to the shaft.

In some implementations, the dispensing device can be built from a material that is impact-resistant and environment-tolerant. Non-limiting examples of material that can be used to form the dispensing device include Acrylonitrile butadiene styrene (ABS), polycarbonate, acetyl, polypropylene, polyethylene, polyvinyl chloride (PVC), aluminum, steel or other material, including blends of the above or including filler material such as glass or carbon fiber to alter the material properties.

Figure 24:
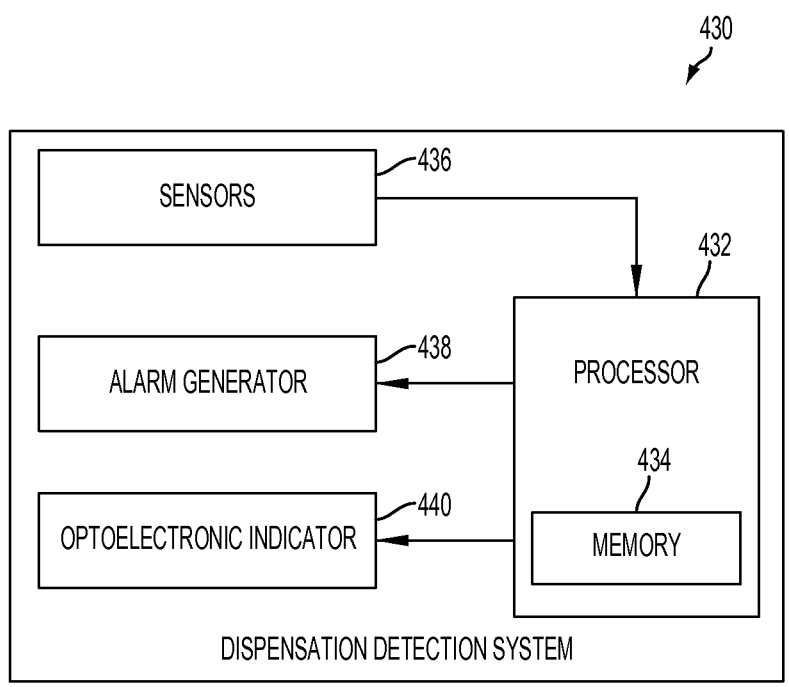
FIG. 24 is an example block diagram of an example dispensation detection system.

In one embodiment, the dispensing device is configured to detect the dispensation of articles using a dispensation detection system. FIG. 24 is an example block diagram of an embodiment of a dispensation detection system 430 implemented according to aspects of the present technique. The dispensation detection system 430 includes a processor 432, alarm generator 438, sensors 436 and optoelectronic indicator 440.

In some embodiments sensors 436, are electromechanical devices that are coupled to one or more components of the dispensing device 10 and are configured to generate a signal. The signal corresponds to a displacement of the carousel 20 with respect to the base member 12. In one embodiment, the electromechanical devices are disposed inside the dispensing device 10. For example, the electromechanical devices are disposed on a base member 12 and/or a carousel 20 of the dispensing device.

In one embodiment, the sensor 436 can be a mechanical switch, which can be configured to alternate between an enable and disable state where each state change corresponds to a displacement of the carousel 20 by one compartment 23. One such example is a snap action limit switch such as the Panasonic ESE-181101.

Figure 25:
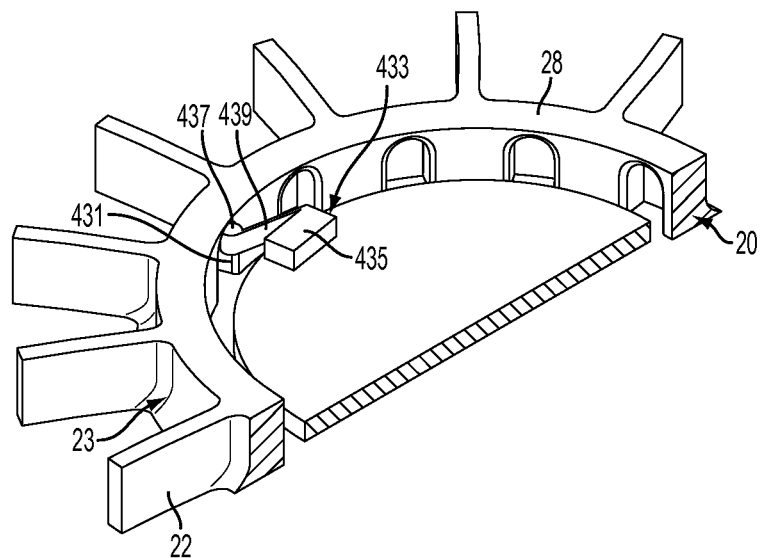
FIG. 25 is an example cut-away top perspective view of a partial section of a carousel of the dispensing device of FIG. 1 in a first position, with an illustrative example of an example mechanical switch.

Referring to FIG. 25, an example embodiment of a mechanical switch 433 includes a body 435 and a roller 437 positioned on the end of a lever 439. When the carousel 20 is at rest, the roller 437 is positioned inside a recess 431 on the inner surface of the carousel 424 and this position corresponds to the switch being OFF.

Figure 26:
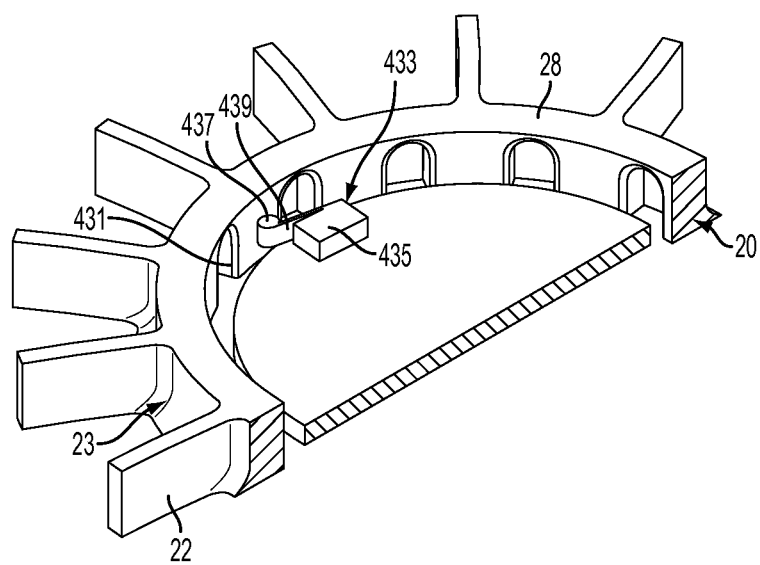
FIG. 26, is the carousel of FIG. 4 shown in a second position.

Referring to FIG. 26, as the carousel 20 is rotated, the roller 437 rides along the inner surface, leaving the recess 431. As it does so, the lever 439 moves toward the body 435 of the mechanical switch 433, closing the circuit and providing an ON signal to the processing circuitry. When the carousel 20 has moved by one compartment 23, the roller 437 is in the next recess 431, and is again in an OFF position.

In another embodiment, the sensors 436 can be a plurality of magnets and a plurality of magnetic sensors. The magnetic sensors can be configured to detect a change in the electromagnetic field generated by the magnets based on the movement of the carousel. In one embodiment, the number of magnets used is less than or equal to the number of compartments and the numbers of magnetic sensors are different from the number of magnets.

In some embodiments, the sensors 436 are optical sensors coupled to the base member 12 and configured to sense a change in a reflective pattern disposed on a wall of each compartment 23 to determine a state of the respective compartment 23. Example states of the compartment are: "empty," "partially full," and "full." One example of an optical sensor is an infrared (IR) detector, which is often used in conjunction with an IR emitter, and detects when an IR source is blocked, reflected, or diminished. An example of an IR emitter/detector sensor is a reflective sensor such as the Honeywell HIX1395, which is a package that emits IR and then detects it in the same package.

Figure 27:
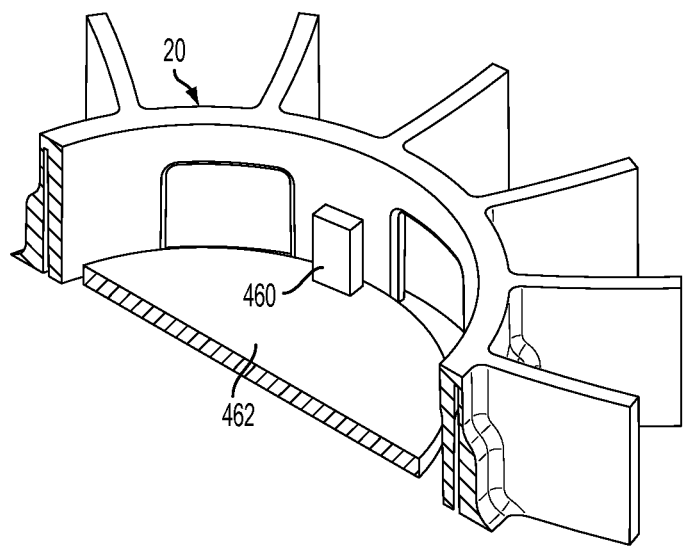
FIG. 27, is an example cut-away top perspective view of a partial section of a carousel of the dispensing device of FIG. 1, in a first position, with an illustrative example of an example optical switch.
Figure 28:
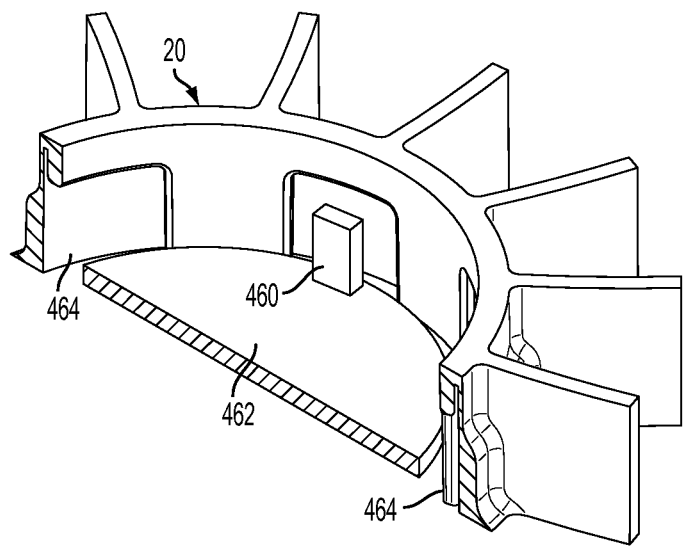
FIG. 28, is the carousel of FIG. 6 shown in a second position.

Referring to FIGS. 27 and 28, in some implementations, the optical sensor includes an IR emitter/detector 460 mounted above the circuit board 462 to detect features 464 in the carousel 20. These features 464 are either "shiny" with high IR reflective properties (such as mylar tape adhered to the surface, or a sheet of aluminum placed into a slot), or "dull" with low IR reflectivity (and possible IR absorption) properties (such as the plastic material of the carousel 20). When the carousel 20 is rotated relative to the sensor, "shiny" features will generate a "1" in the sensor, and "dull" features will generate a "0".

In some implementations, the optical sensor may be used to perform analog measurements (which will get translated to a digital value). In an example scenario, instead of the IR emitter/detector shining against a reflective or non-reflective surface (0 or 1), it could instead shine against a surface that has partial reflectivity. The IR detector could then be read based on the resolution of the sensing system and could measure analog values. In an example scenario, the high resolution of the sensing system and the microcontroller, could differentiate between one thousand and twenty-four (1024) different values from a single reflective surface. In practice, this can be envisioned as the reflective markers not only being white (1024="1") and black (0="0"), but also being a color in a gray scale, e.g. intermediate gray colors (256, 784, etc. . . . ).

Referring again to FIG. 24, processor 432 is configured to process the signal generated by the sensors 436. The signal is processed to determine information such as time of displacement of the carousel 20, the compartment 23 that was accessed and state of the compartment 23 (e.g. empty, partially full, full as described above). In some implementations, the signal could be processed to determine whether compartment 23 had been emptied. Processor 432 includes memory 434 where such information is stored and can be retrieved when required. Memory 434 may also be used to store user data, user schedule data, and the like.

Processor 432 is further configured to periodically transmit a time log to a computing device, wherein the time log comprises a set of time data corresponding to the time at which the carousel is rotated. Processor 432 is further configured to store state information related to the accessed compartments 23. Further, an alarm generator 438 is coupled to the processor 432 and is configured to generate reminders based on the data stored in the memory 434. Non-limiting examples of reminders may be acoustic signals, optical signals, vibrations, or a combination thereof.

In some implementations, the dispensing detecting system can include an optoelectronic indicator 440 configured to indicate to a user, a state of a particular compartment 23. In an example implementation, the optoelectronic indicator 440 is disposed on the cover 18 of the dispensing device 10. Non-limiting example states of a particular compartment 23 that can be determined from the optoelectronic indicator 440 are "empty," "partially full," and "full."

In one embodiment, each compartment 23 of the dispensing device is identified with a marker (e.g. "1"), and a transition state between compartments is identified with a different marker (e.g. "0"). Upon rotation of the carousel 20, the processor 432 is configured to detect a transition from one compartment 23 to the next to determine whether the next compartment has been accessed. In one embodiment, the processor 432 implements a relative encoding scheme to keep count of the number of compartments 23 that have been accessed as well as which compartment 23 is currently available for access.

In another embodiment, each compartment 23 of the dispensing device is identified with a unique identifier. Upon rotation of the carousel 20, the processor 432 is configured to execute an encoding scheme to determine the unique identifier of the compartment 23 accessed by a user. In one embodiment, the processor 432 implements an absolute encoding scheme to determine the unique identifier of the compartment 23 which is being accessed. In some implementations, for example where there are sixteen compartments, the unique identifier is a four-bit code. In other implementations the value of the bit code may change depending up on the number of compartments. In an example scenario where the dispensing device includes thirty-two compartments the unique identifier is a five bit code or a six bit code.

Figure 29:
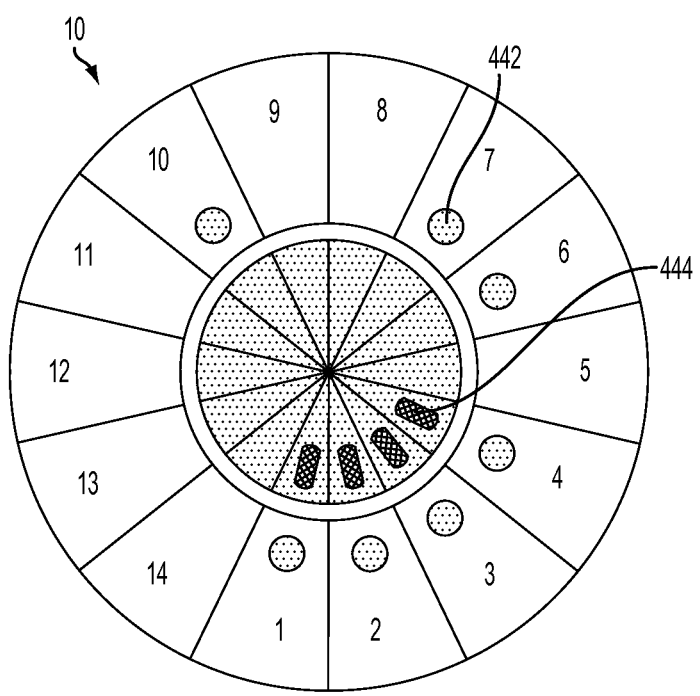
FIG. 29 is an example diagram of arrangement of magnets and sensors for an example absolute encoding scheme.
Figure 30:
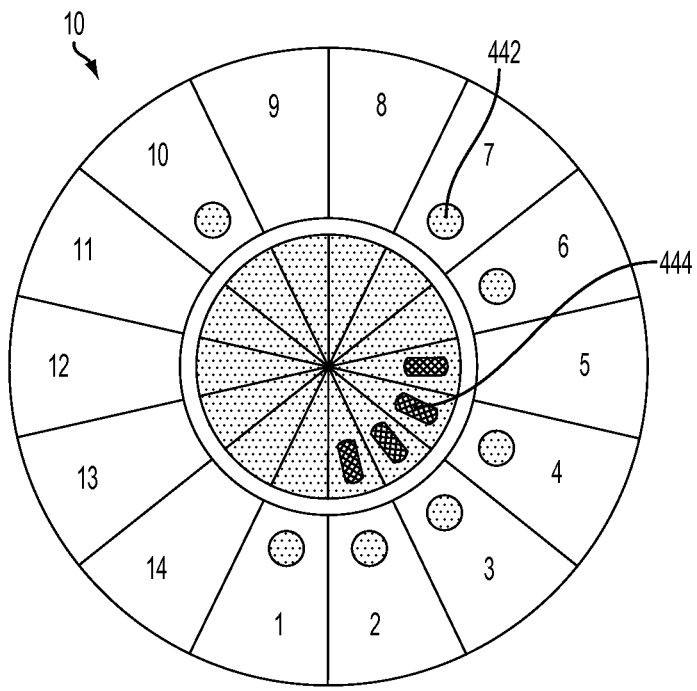
FIG. 30 is an example diagram which refers to the movement of a carousel by one compartment.
Figure 31:
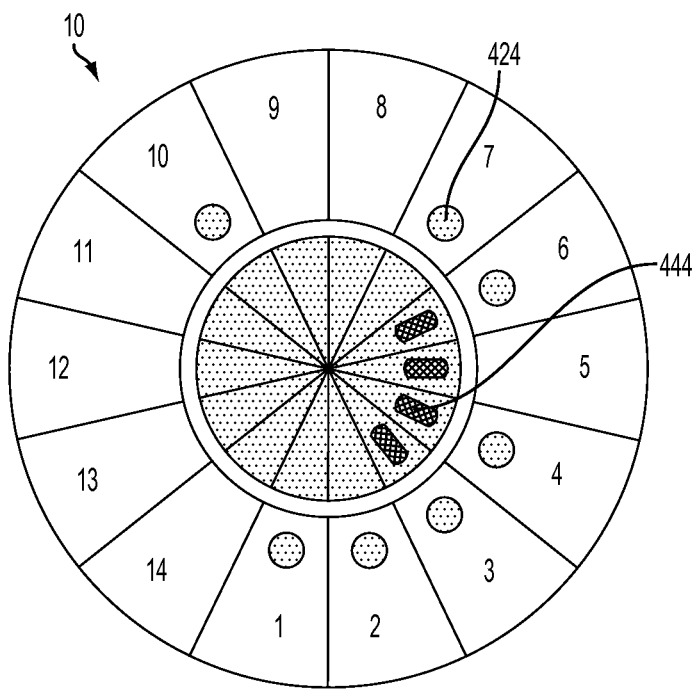
FIG. 31 is an example diagram which refers to the movement of a carousel by another compartment.

Referring to FIGS. 29-31, in an example implementation, the absolute encoding scheme can be implemented by placing four magnetic sensors 444 on the base member 12 and seven magnets 442 on the carousel 20. The combination of the magnetic sensors 442 and magnets 444 are used as a unique identifier for each compartment. In some implementations, the absolute encoding scheme may be achieved with a similar number of IR sensors and shiny/dull surfaces corresponding to the compartment locations, or other sensor mechanisms.

In an example encoding scheme, when a magnetic sensor 442 is aligned with a magnet 444, the magnetic sensor reads '1'. Similarly, when a magnetic sensor 444 and magnet 442 are not aligned, the magnetic sensor reads '0'. Referring to FIGS. 29 and 30, as the carousel rotates the alignment of particular magnets 442 with respect to particular magnetic sensors 444 changes accordingly. Each rotation of carousel results in different combinations of alignments of magnets 444 and magnetic sensor 442 thereby generating a unique four bit pattern of '1's and '0's. The unique patterns of '1's and '0's can be used to specifically identify each compartment. As the carousel 20 is rotated about the base, the magnetic sensor 444 reading changes, and gives a unique encoding that can be used to identify each compartment, which can be seen from Table 1, below. In some implementations, the foregoing example encoding scheme may be achieved with a similar number of IR sensors and shiny/dull surfaces corresponding to the compartment locations, or other sensor mechanisms.

TABLE 1

| Generated Pattern | Compartment |
|---|---|
| 1111 | Compartment 1 |
| 1110 | Compartment 2 |
| 1101 | Compartment 3 |
| 1011 | Compartment 4 |
| 0110 | Compartment 5 |
| 1100 | Compartment 6 |
| 1001 | Compartment 7 |
| 0010 | Compartment 8 |
| 0100 | Compartment 9 |
| 1000 | Compartment 10 |
| 0000 | Compartment 11 |
| 0001 | Compartment 12 |
| 0011 | Compartment 13 |
| 0111 | Compartment 14 |

Non-limiting examples of magnets include axially-magnetized Neodymium disc magnets such as 1/8' Dia×1/16" Thick Rare Earth Magnet Disc, Licensed NdFeB, Grade N50, Ni—Cu—Ni (Silver in Color) Plated, Magnetized Axially Magnetized, Poles On Flat Face. Example sensors include Hall effect sensors or reed switch sensors such as the Coto Technology reed switch.

Figure 32:
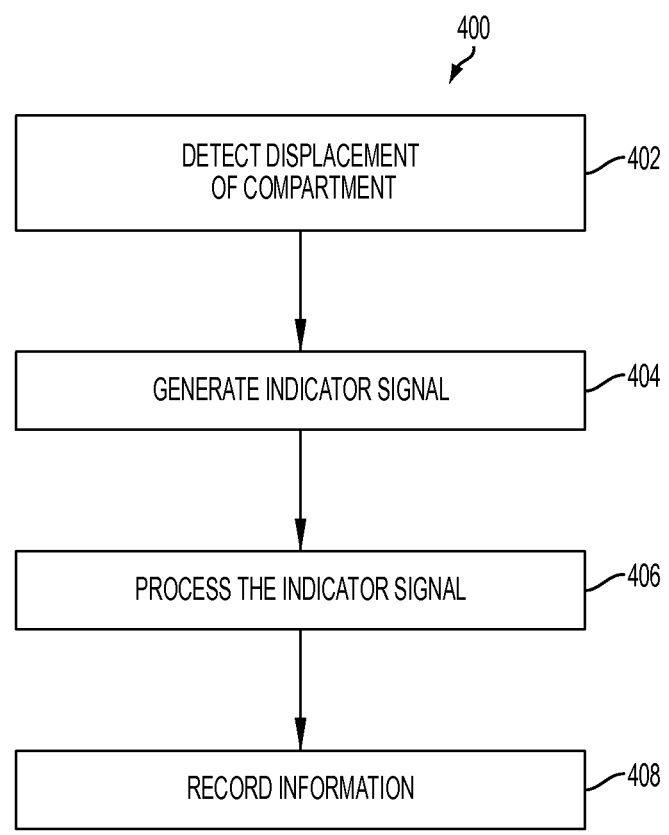
FIG. 32 is an example flow diagram of an embodiment of a dispensation detection system.

FIG. 32 is a flow chart illustrating one method of detecting dispensation from a dispensing device 10. A dispensation detection system is implemented within the dispensing device 10 to detect dispensation. At step 402, a displacement of the carousel 20 is detected. In one embodiment, the carousel 20 rotates around a center of the base member 12.

At step 404, an indicator signal is generated. In one embodiment, the indicator signal corresponds to a mechanical displacement of the carousel 20 from a first position to a second position. Each displacement of the carousel 20 corresponds to movement of a single compartment 23.

At step 406, the indicator signal is processed to determine a time at which the carousel 20 was displaced. In one embodiment, the indicator signal further provides information regarding which compartment 23 was accessed.

At step 408, the information extracted from the indicator signal is stored. In a further embodiment, the information is transmitted to a computing system that is coupled to the dispensing device 10. Further, the information is also used to send alerts to multiple users associated with the dispensing device 10.

The techniques described above have several advantages including accurately determining a time at which the dispensing device was accessed thereby enabling a user to closely monitor the dispensing device. Also, since each compartment 23 of the dispensing device 10 can be specifically identified, the articles that were accessed from a particular compartment can also be closely monitored. Such systems can be particularly helpful in the administration of medication.

In the foregoing detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claims, and in the absence of such recitation no such intent is present.

Some example embodiments reference a pill box used for dispensing medicines, however it should be understood that the techniques described herein may be applied in any type of dispensing device that is used to dispense articles stored within in a controlled manner.

For example, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"). The same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

While only certain features of several embodiments have been illustrated and described herein, many modifications and changes will occur to those skilled in the art. It is, therefore, to be understood that the appended claims are intended to cover all such modifications and changes as fall within the true spirit of the invention.

What is claimed is:

1. A dispensing device, comprising:
   a base member;
   a carousel coupled to the base member and configured to rotate about the base member;
   a cover disposed on a top portion of the carousel;
   a linking component disposed on one of: the cover and the base member; and
   a securing mechanism disposed on the dispensing device and configured to prevent unauthorized access to contents stored within the dispensing device, wherein the securing mechanism comprises:
      at least one sensor operatively coupled to the linking component; and at least one alarm generator operatively coupled to the at least one sensor, the alarm generator configured to generate an alarm signal in response to detection, by the at least one sensor, of displacement of the cover.

2. The dispensing device of claim 1, wherein the alarm signal is one or more of: an acoustic indicator signal and a visual indicator signal.

3. The dispensing device of claim 1, wherein the detection, by the at least one sensor, comprises detecting that the linking component is decoupled from the at least one sensor.

4. The dispensing device of claim 1, wherein the linking component comprises an electronic device or a mechanical component.

5. The dispensing device of claim 1, wherein the linking component comprises at least one magnet, and wherein upon displacement of the cover, the at least one sensor is configured to detect a change in electromagnetic field generated by the at least one magnet.

6. The dispensing device of claim 3, further comprising processing circuitry disposed within the dispensing device and configured to record a time at which the linking component is decoupled from the at least one sensor.

7. The dispensing device of claim 6, wherein the processing circuitry is further configured to transmit a time log, wherein the time log comprises a first time at which the cover was displaced and a second time at which the carousel was rotated.

8. The dispensing device of claim 1, further comprising a lid configured to enclose the base member and the carousel, wherein the cover is disposed on the lid.

9. The dispensing device of claim 8, wherein the securing mechanism further comprises a security component formed by an inner wall extending upwards from a base plate of the base member and an outer wall of the lid, wherein the inner wall of the base member and an outer wall of the lid overlap when enclosing the carousel.

10. The dispensing device of claim 1, wherein the securing mechanism further comprises at least one security fastener configured to mechanically fasten the cover to the base member.

11. The dispensing device of claim 1, further comprising visual indicators disposed on the dispensing device.

12. A dispensing device, comprising:
a base member;
a carousel coupled to the base member and configured to rotate about the base member;
a lid configured to enclose the base member and the carousel;
a cover disposed on the lid; and
a tamper detection device comprising:
at least one electromechanical component disposed within the dispensing device; and
at least one electromechanical sensor corresponding to the electromechanical component and configured to generate an alarm signal in response to detection, by the at least one electromechanical sensor, of displacement of the cover.

13. The dispensing device of claim 12, wherein the electromechanical component is a magnet and electromechanical sensor is a magnetic sensor, and wherein the magnetic sensor is configured to detect a change in electromagnetic field generated by the magnet in response to the displacement of the cover.

14. The dispensing device of claim 12, wherein the electromechanical component is an optical emitter and electromechanical sensor is an optical sensor; wherein the optical sensor is configured to detect an optical change in optical path of the optical emitter in response to the displacement of the cover.

15. The dispensing device of claim 12, further comprising processing circuitry disposed within the dispensing device and configured to store a time log, wherein the time log comprises a time at which the cover was displaced.

* * * * *